US010633706B2

(12) United States Patent
Ebenstein et al.

(10) Patent No.: US 10,633,706 B2
(45) Date of Patent: Apr. 28, 2020

(54) ANALYSIS OF METHYLATION STATUS AND COPY NUMBER

(71) Applicants: Ramot at Tel-Aviv University Ltd., Tel-Aviv (IL); Rheinisch-Westfälische Technische Hochschule (RWTH) Aachen, Aachen (DE)

(72) Inventors: Yuval Ebenstein, Yavne (IL); Elmar Weinhold, Aachen (DE); Assaf Grunwald, Tel-Aviv (IL); Tslil Gabrieli, Tel-Aviv (IL)

(73) Assignees: Ramot at Tel-Aviv University Ltd., Tel-Aviv (IL); Rheinisch-Westfälische Technische Hochschule (RWTH) Aaachen, Aachen (DE)

( * ) Notice: Subject to any disclaimer, the term of this patent is extended or adjusted under 35 U.S.C. 154(b) by 0 days.

(21) Appl. No.: 16/324,576

(22) PCT Filed: Aug. 10, 2017

(86) PCT No.: PCT/IL2017/050889
§ 371 (c)(1),
(2) Date: Feb. 11, 2019

(87) PCT Pub. No.: WO2018/029693
PCT Pub. Date: Feb. 15, 2018

(65) Prior Publication Data
US 2019/0194755 A1   Jun. 27, 2019

Related U.S. Application Data

(60) Provisional application No. 62/372,879, filed on Aug. 10, 2016.

(51) Int. Cl.
*C12Q 1/6883* (2018.01)
*C12Q 1/683* (2018.01)

(52) U.S. Cl.
CPC .......... *C12Q 1/6883* (2013.01); *C12Q 1/683* (2013.01); *C12Q 2600/154* (2013.01); *C12Y 301/21004* (2013.01)

(58) Field of Classification Search
None
See application file for complete search history.

(56) References Cited

U.S. PATENT DOCUMENTS

| 7,960,105 | B2 | 6/2011 | Schwartz et al. | |
| 2010/0137154 | A1* | 6/2010 | Ach | C12Q 1/6827 506/9 |
| 2013/0210007 | A1* | 8/2013 | Godler | C12Q 1/6883 435/6.11 |
| 2015/0368706 | A1* | 12/2015 | Cao | C12Q 1/6809 506/4 |

FOREIGN PATENT DOCUMENTS

| WO | WO 00/06587 | 2/2000 |
| WO | WO 2005/121361 | 12/2005 |
| WO | WO 2006/108678 | 10/2006 |
| WO | WO 2010/035140 | 4/2010 |
| WO | WO 2014/113843 | 7/2014 |
| WO | WO 2014/191981 | 12/2014 |
| WO | WO 2015/126840 | 8/2015 |
| WO | WO 2016/057648 | 4/2016 |
| WO | WO 2018/029693 | 2/2018 |

OTHER PUBLICATIONS

Lukinavicius et al (J. Am. Chem. Soc. 2007. 129: 2758-2759.*
International Search Report and the Written Opinion Dated Nov. 15, 2017 From the International Searching Authority Re. Application No. PCT/IL2017/050889. (17 Pages).
Gilboa et al. "Single-Molecule DNA Methylation Quantification Using Electro-Optical Sensing in Solid-State Nanopores", ACS Nano, 10(9): 8861-8870, Aug. 31, 2016.
Grunwald et al. "Bacteriophage Strain Typing by Rapid Single Molecule Analysis", Nucleic Acids Research, 43(18): e117-1-e117-8, May 27, 2015.
Grunwald et al. "Reduced Representation Optical Methylation Mapping (R2OM2)", BioRxiv, 113522: 1-20, Posted Online Mar. 3, 2017.
Hanz et al. "Sequence-Specific Labeling of Nucleic Acids and Proteins With Methyltransferases and Cofactor Analogues", Journal of Visualized Experiments, 93: e52014-1-e52014-10, Nov. 2014.
Kunkel et al. "A 7-Deazaadenosylaziridine Cofactor for Sequence-Specific Labeling of DNA by the DNA Cytosine-C5 Methyltransferase M.HhaI", Molecules, 20: 20805-20822, Nov. 23, 2015.
Lemmers et al. "Inter-Individual Differences in CpG Methylation at D4Z4 Correlate With Clinical Variability in FSHD1 and FSHD2", Human Molecular Genetics, 24(3): 659-669, Published Online Sep. 25, 2014. Abstract.
Nelson et al. "Site-Specific Methylation: Effect on DNA Modification Methyltransferases and Restriction Endonucleases", Nucleic Acids Research, 19(Suppl.): 2045-2071, Apr. 25, 1991.
Todorov et al. "A Unified Rapid PCR Method for Detection of Normal and Expanded Trinucleotide alleles of CAG Repeats in Huntington Chorea and CGG Repeats in Fragile X Syndrome", Molecular Biotechnology, 45(2): 150-154, Published Online Mar. 9, 2010.
Supplementary European Search Report and the European Search Opinion dated Jan. 24, 2020 From the European Patent Office Re. Application No. 17838933.4. (9 Pages).
Cao et al. "Rapid Detection of Structural Variation in A Human Genome Using Nanochannel-Based Genome Mapping Technology", GigaScience, XP021207188, 3(1): 34-1-34-11, Published Online Dec. 30, 2014.
Levy-Sakin et al. "Beyond Sequencing: Optical Mapping of DNA in the Age of Nanotechnology and Nanoscopy", Current Opinion in Biotechnology, XP055657083, 24(4): 690-698, Available Online Feb. 18, 2013.
McCaffrey et al. "CRISPR-CAS9 D10A Nickase Target-Specific Fluorescent Labeling of Double Strand DNA for Whole Genome Mapping and Structural Variation Analysis", Nucleic Acids Research, XP055351972, 44(2): e11-1-e11-8, Published Online Oct. 19, 2015.

* cited by examiner

*Primary Examiner* — Carla J Myers

(57) ABSTRACT

A method of diagnosing a disease associated with a DNA repeat sequence is disclosed. The method comprises:
(a) determining the number of repeats of a DNA sequence in DNA molecules of a sample of the subject; and
(b) determining the CpG methylation status of the DNA molecules, wherein the number of repeats of the DNA sequence and the CpG methylation status of the DNA molecules is indicative of the disease.

23 Claims, 6 Drawing Sheets
(6 of 6 Drawing Sheet(s) Filed in Color)
Specification includes a Sequence Listing.

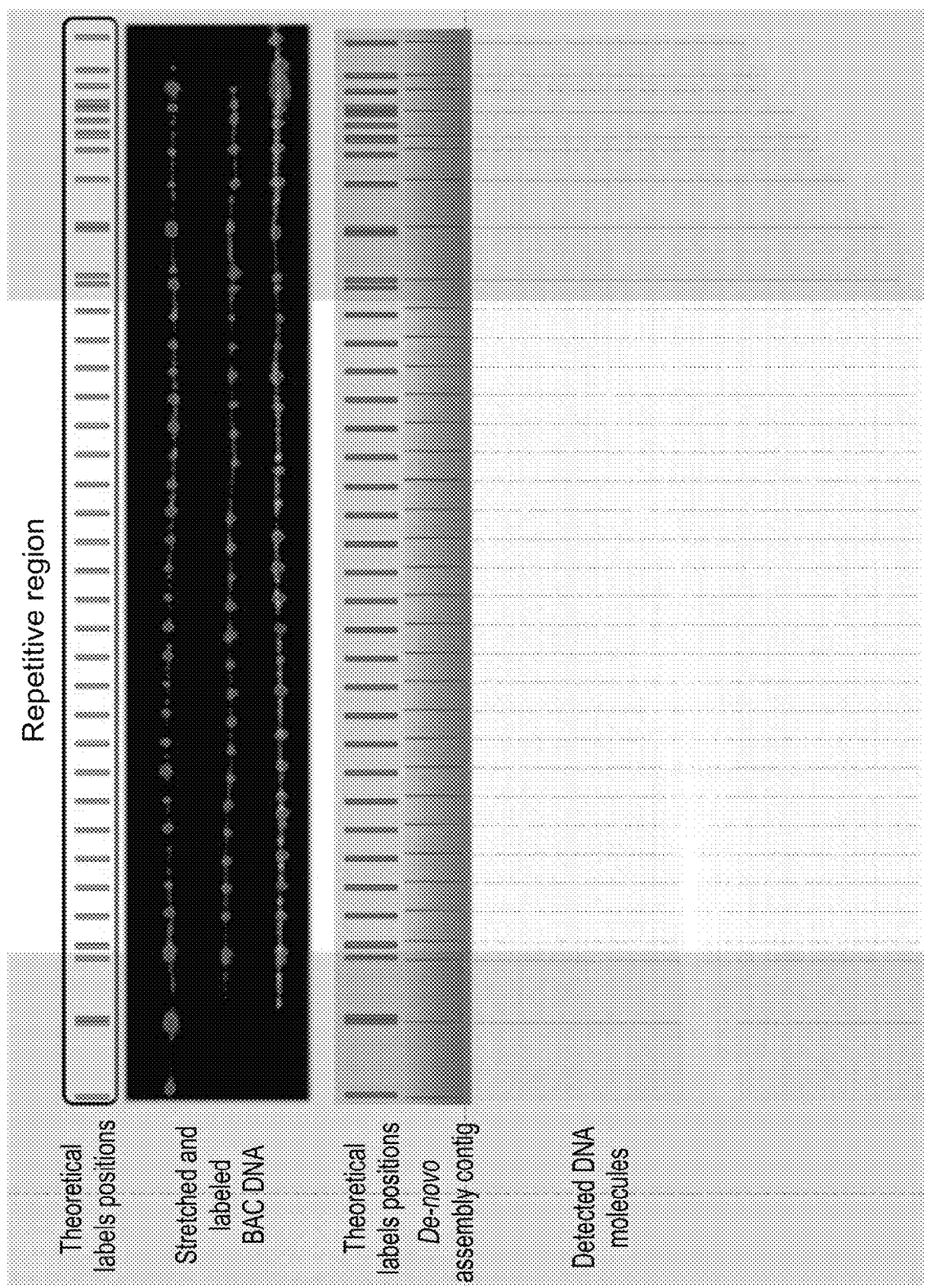

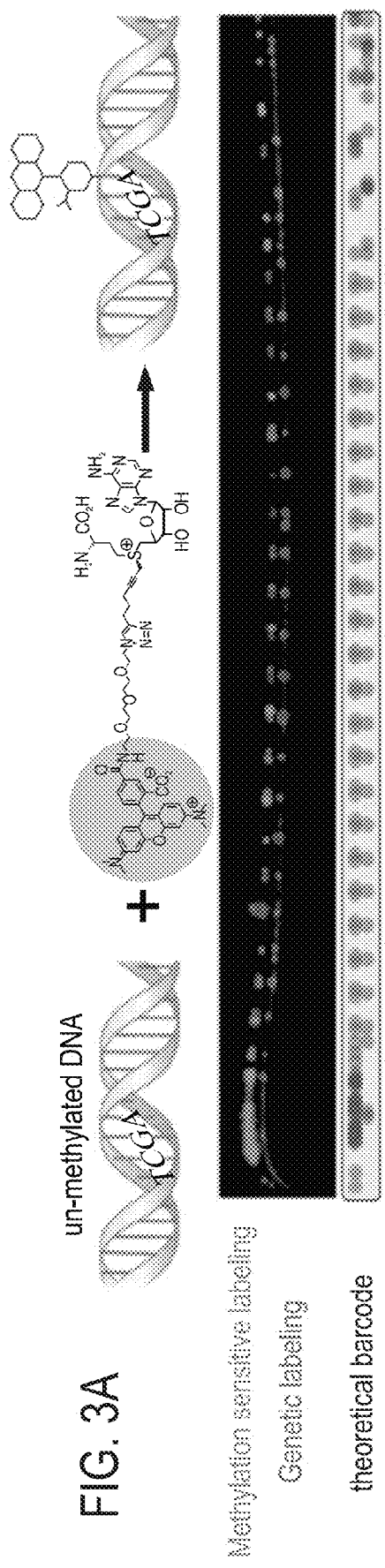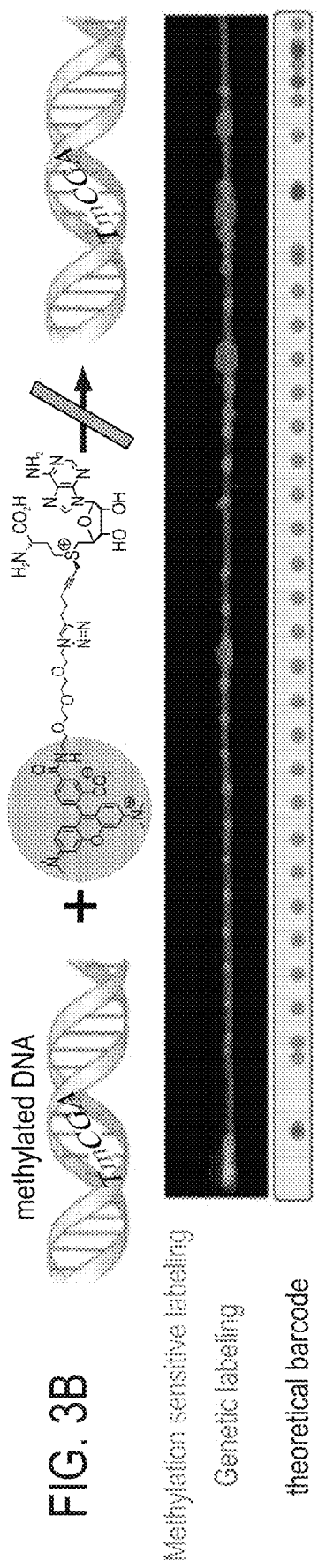

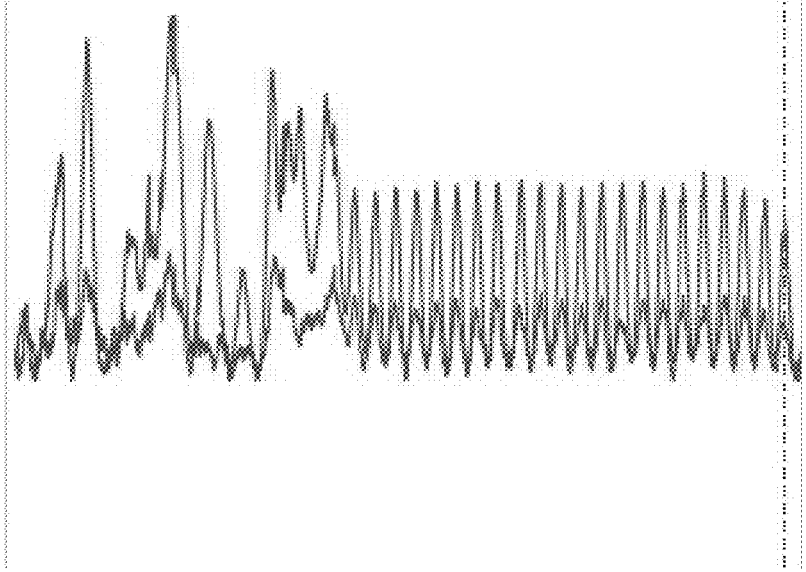

DNA from healthy donor / DNA from cll donor

Chr3: 40.76M-41.23M
493kbp

ANALYSIS OF METHYLATION STATUS AND COPY NUMBER

RELATED APPLICATIONS

This application is a National Phase of PCT Patent Application No. PCT/IL2017/050889 having International filing date of Aug. 10, 2017, which claims the benefit of priority under 35 U.S.C. § 119(e) of U.S. Provisional Patent Application No. 62/372,879 filed on Aug. 10, 2016. The contents of the above applications are all incorporated by reference as if fully set forth herein in their entirety.

SEQUENCE LISTING STATEMENT

The ASCII file, entitled 76484SequenceListing.txt, created on Feb. 11, 2019, comprising 4,774 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to molecular biology and, more particularly, but not exclusively, to simultaneous copy number quantification and DNA methylation detection.

Nearly half of the human genome is composed of DNA repeats: homologous DNA fragments, exhibiting identity (or great similarity) to each other, that lay along varying stretches of the genome. The length of a single repeat unit may vary between one and millions of bases and repetitive genomic regions may consist of two to millions of copies. Repeats are divided into two types: tandem repeats, which are composed of concatenated units forming a continuous repetitive region, and interspersed repeats, which are scattered along the entire genome. Many repetitive regions have been shown to be involved in gene regulation, genome stability and disease. Examples include telomeres and the CAG repeats related to Huntington's disease, both of which are tandem repeats with direct functional impact on cellular activity and fate. Large populations of repeats are mobile elements, which can transpose across the genome and perform homologous recombination events, promoting dynamic genomic transformations. Thus, it is believed that repetitive elements play a major role in human evolution, allowing the exponential speed that characterizes the development of our species. The dynamic nature of repetitive elements also leads to variations both among different individuals and between different cells of the same individual.

A second dimension of dynamics is added to repeat arrays by their methylation status. CpG methylation is a major epigenetic modification responsible for genetic regulation and often associated with the promoter region of genes. It has been shown that methylation levels of DNA repeats are correlated with various types of cancer and its severity. Consequently, a given repeat array may vary not only in the number of units but also in the methylation status of each of its units.

Despite their significance, repetitive elements are almost inaccessible to Next Generation Sequencing (NGS) methods. This is due to the fact that current NGS techniques employ random fragmentation of genomic material and only sequence relatively short "reads" that do not span the full repetitive array. Assembly of these short reads into a long contiguous sequence is fundamentally limited because assembly algorithms cannot distinguish between identical sequence copies that comprise the investigated region. Hence, despite the emergence of new sequencing technologies and sample preparation techniques, the study of repetitive regions is still limited by the typical read length (~50-500 bp) of current gold-standard NGS platforms. With this in mind, it is possible that some of the many sequence duplications that have been discovered are in fact longer repetitive elements.

There are several alternative methods for copy number analysis, including southern blotting, quantitative PCR and comparative genomic hybridization assays. These methods offer indirect, relative information, making them prone to bias, and typically suffer from resolution problems in size estimation. In addition, similar to NGS, they are based on "bulk" measurements, resulting in averaged information, which often masks intercellular variability. While these methods offer a partial solution for quantification of repeats, studying the methylation status of repeat arrays remains a major stumbling block. Bisulfite sequencing, the "gold-standard" method for CpG methylation studies, is NGS-based and thus limited in the information it can provide on repetitive sequences. These limitations become critical if the length of a repeat unit is longer than the length of the sequencing read. In such cases, only parts of the first and last repeat units can be addressed for methylation studies. As a result, there is currently no method capable of analyzing methylation patterns of repeat arrays.

One of the most striking and well-studied examples of a pathogenic repeat region is the D4Z4 macrosatellite array. D4Z4 is a 3.3-kbp long repeat unit organized in an array at the subtelomeric region of chromosome 4q. This array is directly linked to facioscapulohumeral muscular dystrophy (FSHD), the third most common form of muscular dystrophy with a world-wide prevalence of 1 in 20,000 (1 in 7,500 in Europe). This disease is characterized by progressive weakening of selective facial and limb-girdle muscle groups. The autosomal dominant genotype of FSHD is a constellation in the D4Z4 array; while healthy individuals carry more than 10 copies of this repeat, carriers would possess less than 10 repeats (FIG. 1A). This reduction is believed to have an epigenetic effect, altering the repression of the DUX4 gene, leading to expression of this, typically silenced, transcription factor in patients' muscle cells. Recent studies show that some patients possess a normal number of D4Z4 repeat units but still display FSHD symptoms. The genotype for this variant of the disease, which is termed FSHD2, shows decreased DNA methylation of the typically hypermethylated D4Z4 repeat array (FIG. 1A). Moreover, methylation seems to play a significant role in the activation of the disease, as individuals who possess a genetically pathogenic allele, containing less than 10 D4Z4 repeats, do not manifest FSHD symptoms if the repeats are hypermethylated (FIG. 1A). Studies on FSHD patients and their families show that a high percentage (~30%) of patients do not inherit the disease, but rather develop de-novo mutations, perhaps due to recombination events between the chromosome 4 repeat array and a very similar (non-pathogenic) array that lies in chromosome 10. Many of these patients exhibit somatic mosaicism, meaning that they have different numbers of repeats in different cells, which further complicates diagnosis by currently available techniques.

Optical mapping of DNA stands out as an attractive approach for studying large genomic arrangements such as repeat arrays. The approach consists of a set of techniques for stretching long genomic fragments, followed by imaging of these fragments using fluorescence microscopy. Image processing is then used to read out a low-resolution physical barcode along the molecules that provides genetic information such as the size and number of large repeat units. Furthermore, the technique offers access to additional genomic information such as DNA damage lesions and epigenetic marks. These attributes have driven the commercialization of several optical mapping approaches, and facilitated the development of a clinical genetic test for FSHD [Nguyen et al., Ann. Neurol. 2011, 70, 627-633]. Recently, whole genome optical mapping has been performed by electrokinetically stretching barcoded DNA molecules in highly parallel nanochannel arrays. This technique, commercialized by BionanoGenomics Inc., is capable of automated copy number analysis on a genome scale [Cao, H. Gigascience 2014, 3, 34; Huichalaf, C. et al., PLoS One 2014, 9, e115278; Mostovoy, Y Nat. Methods 2016, 12-17]. However, commercial protocols do not support detection of the D4Z4 macrosatellite repeat array.

Additional background art includes Kunkel, F.; Lurz, R.; Weinhold, E. A Molecules 2015, 20, 20805-20822; Grunwald, A.; et al. Nucleic Acids Res. 2015, 43, e117 and Nelson, M et al., Nucleic Acids Res. 1991, 19, 2045-2071.

SUMMARY OF THE INVENTION

According to an aspect of some embodiments of the present invention there is provided a method of diagnosing a disease associated with a DNA repeat sequence comprising:

(a) determining the number of repeats of a DNA sequence in DNA molecules of a sample of the subject; and (b) determining the CpG methylation status of the DNA molecules, wherein the number of repeats of the DNA sequence and the CpG methylation status of the DNA molecules is indicative of the disease.

According to an aspect of some embodiments of the present invention there is provided a mammalian DNA molecule comprising at least two different detectable moieties, wherein a first detectable moiety of the at least two different detectable moieties specifically labels unmethylated CpG sites and a second detectable moiety of the at least two different detectable moieties specifically labels a DNA sequence other than the CpG site.

According to an aspect of some embodiments of the present invention there is provided a kit comprising:

(i) a methyltransferase enzyme;

(ii) a co-factor of the methyltransferase enzyme which is labeled with a detectable moiety; and (iii) a sequence specific DNA labeling agent.

According to an aspect of some embodiments of the present invention there is provided a method of analyzing the methylation status of a CpG site along a DNA molecule comprising:

(a) contacting the DNA with a methyltransferase enzyme in the presence of a co-factor which is labeled with a detectable moiety under conditions which brings about transfer of the detectable moiety from the co-factor to the DNA;

(b) extending the DNA molecule; and (c) detecting the detectable moiety, wherein the presence of the detectable moiety is indicative of a non-methylated CpG site.

According to further features in the described preferred embodiments, step (b) is effected by contacting the DNA molecules with a methyltransferase (MTase) enzyme in the presence of a co-factor which is labeled with a detectable moiety under conditions which brings about transfer of the detectable moiety from the co-factor to the DNA molecules.

According to further features in the described preferred embodiments, the DNA molecules following the contacting.

According to further features in the described preferred embodiments, the extending is linearly extending.

According to further features in the described preferred embodiments, step (a) is effected by attaching to the DNA molecules a detectable moiety which labels the repeats of the DNA sequence using a sequence-specific DNA labeling agent.

According to further features in the described preferred embodiments, the repeats appear along the DNA molecule more than five times.

According to further features in the described preferred embodiments, the sequence specific DNA labeling agent is a nicking enzyme.

According to further features in the described preferred embodiments, the nicking enzyme is selected from the group consisting of Nb.BsmI, Nb.BvvCI, Nb.BsrDI, Nb.BssSI, Nb.BtsI, Nt.AlwI, Nt.BbvCI, Nt.BsmAI, Nt.BspQI and Nt.BstNBI.

According to further features in the described preferred embodiments, the nicking enzyme is selected from the group consisting of Cas9, TALE and ZFN nickase.

According to further features in the described preferred embodiments, the sequence-specific DNA labeling agent is a CpG-methylation insensitive DNA MTase.

According to further features in the described preferred embodiments, the CpG-methylation insensitive DNA methyltransferase has a double-stranded recognition sequence which does not contain the 5'-CG-3' sequence.

According to further features in the described preferred embodiments, the CpG-methylation insensitive DNA methyltransferase is a DNA adenine methylase (Dam).

According to further features in the described preferred embodiments, the CpG-methylation insensitive DNA methyltransferase is M.EcoDam or a derivative thereof.

According to further features in the described preferred embodiments, the CpG-methylation insensitive DNA methyltransferase is M.BseCI or a derivative thereof.

According to further features in the described preferred embodiments, the MTase is a CpG-methylation sensitive MTase.

According to further features in the described preferred embodiments, the CpG-methylation sensitive MTase is selected from the group consisting of M.TaqI, M.HhaI, M.HpaII, M.MspI, M.SssI and M.MpeI or a derivative thereof.

According to further features in the described preferred embodiments, the CpG-methylation sensitive MTase is M.TaqI or a derivative thereof.

According to further features in the described preferred embodiments, the extending is effected by depositing the DNA molecule on a surface or extending the DNA molecule in a nanochannel.

According to further features in the described preferred embodiments, the co-factor is S-adenosyl-L-methionine or a derivative thereof.

According to further features in the described preferred embodiments, the co-factor is an aziridine co-factor.

According to further features in the described preferred embodiments, the aziridine co-factor is N-adenosylaziridine or 7-deazaadenosylazinidine or a derivative thereof.

According to further features in the described preferred embodiments, the co-factor is a double-activated S-adenosyl-L-methionine or analogue thereof.

According to further features in the described preferred embodiments, the double-activated S-adenosyl-L-methionine is AdoYnTAMRA or AdoYnAtto532.

According to further features in the described preferred embodiments, the detectable moiety comprises a transferable chemical group.

According to further features in the described preferred embodiments, the disease is associated with a DNA repeat sequence which has an altered methylation status.

According to further features in the described preferred embodiments, the disease is facioscapulohumeral muscular dystrophy (FSHD).

According to further features in the described preferred embodiments, the disease is a polyglutamine disease.

According to further features in the described preferred embodiments, the polyglutamine disease is selected from the group consisting of Spinocerebellar ataxia Type 3, Dentatorubropallidoluysian atrophy (DRPLA), Huntington's disease (HD), Spinocerebellar ataxia Type 1, Spinocerebellar ataxia Type 2, Spinocerebellar ataxia Type 6, Spinocerebellar ataxia Type 7 and Spinocerebellar ataxia Type 17.

According to further features in the described preferred embodiments, the detectable moiety is a fluorescent moiety, a phosphorescent moiety and a chemiluminescent moiety.

According to further features in the described preferred embodiments, the DNA repeat sequence comprises a D4Z4 tandem repeat sequence.

According to further features in the described preferred embodiments, the sequence specific DNA labeling agent is a nicking enzyme.

According to further features in the described preferred embodiments, the nicking enzyme is selected from the group consisting of Nb.BsmI, Nb.BvvCI, Nb.BsrDI, Nb.BssSI, Nb.BtsI, Nt.AlwI, Nt.BbvCI, Nt.BsmAI, Nt.BspQI and Nt.BstNBI.

According to further features in the described preferred embodiments, the kit further comprises at least one additional component selected from the group consisting of a DNA polymerase enzyme, fluorescent nucleotides and a DNA ligase enzyme.

According to further features in the described preferred embodiments, the DNA is of mammalian or plant origin.

According to further features in the described preferred embodiments, the extending is linearly extending.

According to further features in the described preferred embodiments, the extending is effected prior to step (a).

According to further features in the described preferred embodiments, the method further comprises attaching to the DNA molecule an additional detectable moiety which labels a sequence of the DNA which is not a CpG site using a DNA labeling agent.

According to further features in the described preferred embodiments, the DNA labeling agent is a sequence-specific DNA labeling agent.

According to further features in the described preferred embodiments, the sequence of the sequence-specific DNA labeling agent is repeated along the DNA molecule more than five times.

According to further features in the described preferred embodiments, the sequence-specific DNA labeling agent is a nicking enzyme.

According to further features in the described preferred embodiments, the nicking enzyme is selected from the group consisting of Nb.BsmI, Nb.BvvCI, Nb.BsrDI, Nb.BssSI, Nb.BtsI, Nt.AlwI, Nt.BbvCI, Nt.BsmAI, Nt.BspQI and Nt.BstNBI.

According to further features in the described preferred embodiments, the sequence-specific DNA labeling agent is a CpG-methylation insensitive DNA MTase.

According to further features in the described preferred embodiments, the CpG-methylation insensitive DNA methyltransferase has a double-stranded recognition sequence which does not contain the 5'-CG-3' sequence.

According to further features in the described preferred embodiments, the CpG-methylation insensitive DNA methyltransferase is a DNA adenine methylase (Dam).

According to further features in the described preferred embodiments, the CpG-methylation insensitive DNA methyltransferase is M.EcoDam or a derivative thereof.

According to further features in the described preferred embodiments, the CpG-methylation insensitive DNA methyltransferase is M.BseCI or a derivative thereof.

According to further features in the described preferred embodiments, the methyltransferase enzyme is a CpG-methylation sensitive MTase.

According to further features in the described preferred embodiments, the CpG-methylation sensitive MTase is selected from the group consisting of M.TaqI, M.HhaI, M.HpaII, M.MspI, M.SssI and M.MpeI or a derivative thereof.

According to further features in the described preferred embodiments, the method does not comprise subjecting the DNA molecule to fragmentation.

According to further features in the described preferred embodiments, the extending is effected by depositing the DNA molecule on a surface or extending the DNA molecule in a nanochannel.

According to further features in the described preferred embodiments, the method further comprises identifying a position of the non-methylated CpG site along the DNA molecule.

According to further features in the described preferred embodiments, the detectable moiety is a fluorescent moiety.

According to further features in the described preferred embodiments, the additional detectable moiety is a fluorescent moiety distinct from the detectable moiety which labels the non-methylated CpG site.

According to further features in the described preferred embodiments, the co-factor is S-adenosyl-L-methionine or a derivative thereof.

According to further features in the described preferred embodiments, the sequence repeats along the DNA more than 5 times.

According to further features in the described preferred embodiments, the first detectable moiety is a fluorescent moiety.

According to further features in the described preferred embodiments, the second detectable moiety is a fluorescent moiety.

According to further features in the described preferred embodiments, the sequence other than the CpG site is GAATGC.

According to further features in the described preferred embodiments, the DNA is extended.

According to further features in the described preferred embodiments, the DNA molecule is a genomic DNA molecule.

According to further features in the described preferred embodiments, the DNA molecule is longer than 20 Kb.

According to further features in the described preferred embodiments, the DNA molecule is longer than 30 Kb.

According to further features in the described preferred embodiments, the DNA molecule is longer than 40 Kb.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1A:
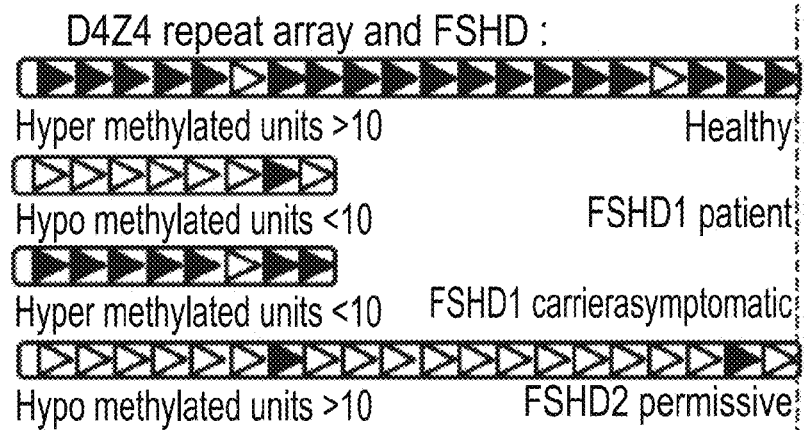
Figure 1B:
Figure 1C:
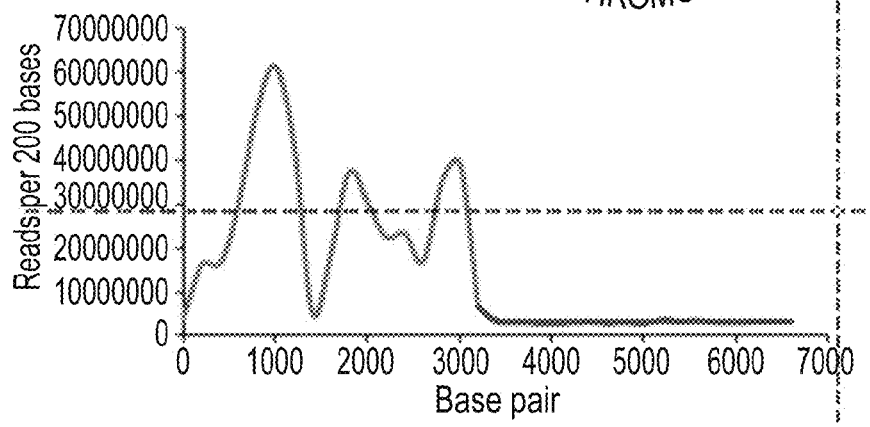
Figure 1D:
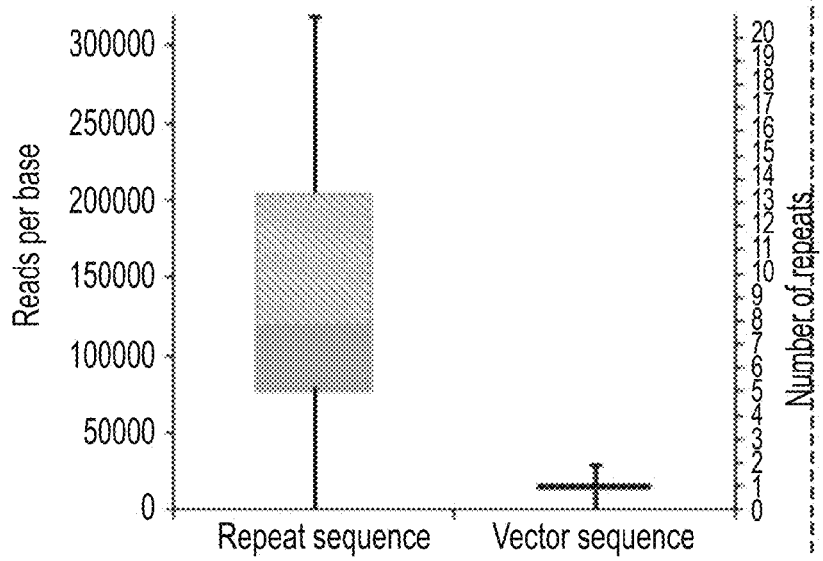

FIGS. 1A-D. FIG. 1A. A schematic representation of the different possible genetic structures of the D4Z4 repeat array, on chromosome 4q35, and the forms of FSHD that they induce. Each triangle represents a repeat unit; the black triangles represent methylated repeat units. From top to bottom: carriers of more than 10 hypermethylated repeats are healthy; carriers of less than 10 hypomethylated repeats are FSHD1 patients; carriers of less than 10 hypermethylated repeats are asymptomatic, and arrays with more than 10 hypomethylated repeats induce FSHD2. FIG. 1B. As a model system, we used bacterial artificial chromosome (BAC) DNA from the CH16 BAC library. This BAC contained an unknown number of the chromosome 4 D4Z4 repeats (shown in green with black triangles), the ~39 kbp genomic DNA on the 5' of the repeat array (shown in green) and the cloning vector pTARBAC6 (shown in blue). FIG. 1C. BAC DNA was sequenced to an ultra-deep coverage (15,000 reads per bp). To assess the number of repeats, reads were aligned to a reference genome containing the sequence of a single repeat and the non-repetitive sequence. A genome coverage track was generated and the number of repeats could be approximated by comparing the average coverage in the repetitive region (plotted in green) to that in the non-repetitive region (plotted in blue). FIG. 1D. Box plots displaying the 25 percentile (the bottom of the lower box), the median (intermediate between lower and upper boxes) and the 75 percentile (the top of the upper box) for coverage values in the repeat region (left plot) and in the non-repetitive region (right plot). The scale on the right is normalized to the median coverage along the non-repetitive region and is intended for assessment of the copy number.

FIGS. 2A-B. Labeling of BAC molecules with the methylation-insensitive Nb.BsmI enzyme. FIG. 2A. A reference map simulating the relative expected locations of labels (highlighted in red) generated by the nicking enzyme Nb.BsmI along a stretched BAC. The repetitive region can be distinguished by virtue of the equally spaced single labels, each representing a single repeat. The non-repetitive regions are highlighted in grey. Representative images of the BAC DNA labeled with Nb.BsmI (red dots) and stretched on modified glass surfaces are presented below the reference. The labeled molecules can be easily aligned to the reference map and the number of repeats can then be quantified by simply counting the equally spaced labels (23 repeats). FIG. 2B. Multiple copies of labeled BAC molecules were stretched and imaged using an Irys device. The detected molecules were de-novo assembled by the Irys software into a contig based on the detected labels. The assembled map shows excellent agreement with the theoretical map generated from the known sequence (displayed in blue). Below the maps are digital representations of the 627 detected molecules used to assemble the map. The yellow lines represent the DNA molecules' contour and the blue dots represent the detected labels. The assembled map contained 23 repeat units, which matched the result obtained from the manual counting of repeat units on the glass-stretched DNA.

FIGS. 3A-B. Methylation detection by dual color labeling. FIG. 3A. From top to bottom: Reaction scheme for labeling of unmethylated DNA by the methyltransferase M.TaqI resulting in green fluorescence. For our FSHD model, the genetic identity and the number of repeat units were provided by labeling with the nicking enzyme Nb.BsmI (red labels). Co-labeling the DNA with the methyltransferase M.TaqI (green labels) indicated that the DNA molecule was unmethylated. The overlay of red and green fluorescence along the molecule aligned well with the expected barcode (the images detecting red and green labels are slightly displaced for better label visibility). FIG. 3B. From top to bottom: DNA methylation within the recognition site of M.TaqI blocks the labeling reaction of the green fluorophore. When the FSHD model was fully methylated prior to labeling, only the red barcode was visible, indicating that the DNA was indeed fully methylated. Similar to the previous case, the red pattern providing the genetic identity and copy number aligned well with the expected barcode.

Figure 4A:
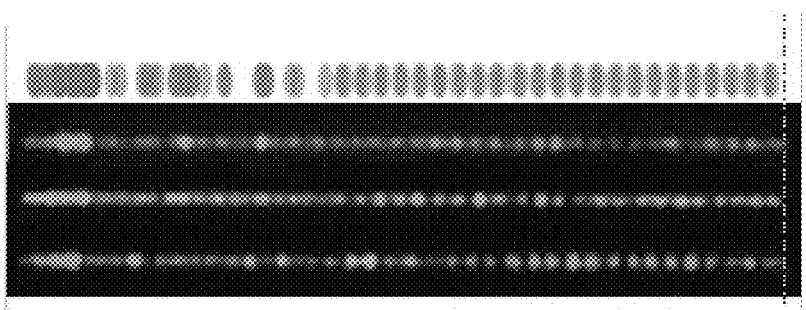
Figure 4B:
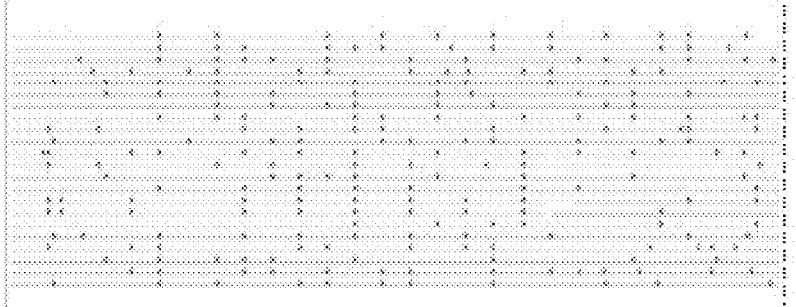
Figure 4C:
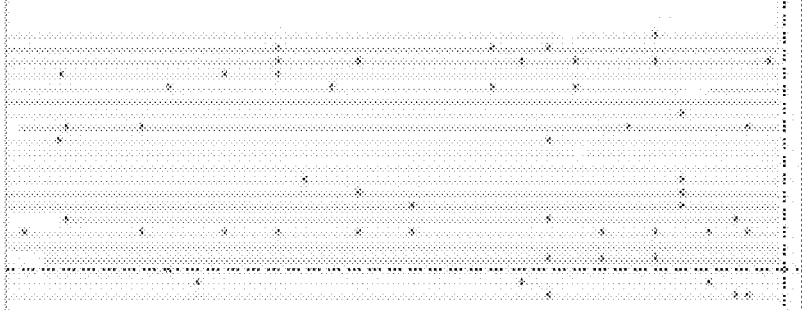

FIGS. 4A-C. High-throughput assessment of methylation levels. FIG. 4A. A reference map (above) simulating the relative expected locations of labels (highlighted in green) generated by the DNA methyltransferase M.TaqI along a stretched FSHD model. Below are images of three unmethylated molecules labeled with M.TaqI, aligned to each other and to the reference map. The repetitive region can be distinguished by virtue of the equally spaced double labels. FIGS. 4B and 4C. Two sets of multiple detected molecules, represented as yellow lines, were aligned to each other and the green methylation patterns were compared. The partially methylated DNA (FIG. 4C) displays significantly fewer labels than the unmethylated DNA (FIG. 4B). FIG. 4C, lower panel. Normalized plots of the integrated values of M.TaqI labels detected by the Irys software along the FSHD model. The red plot is based on 18074 unmethylated DNA molecules and the blue plot is based on 9089 partially methylated DNA molecules. Both plots highly correlated with the expected reference map, allowing detection and study of each individual repeat. The unmethylated data set displays significantly more labels (p-value<$10^{-50}$, t-test).

Figure 5A:
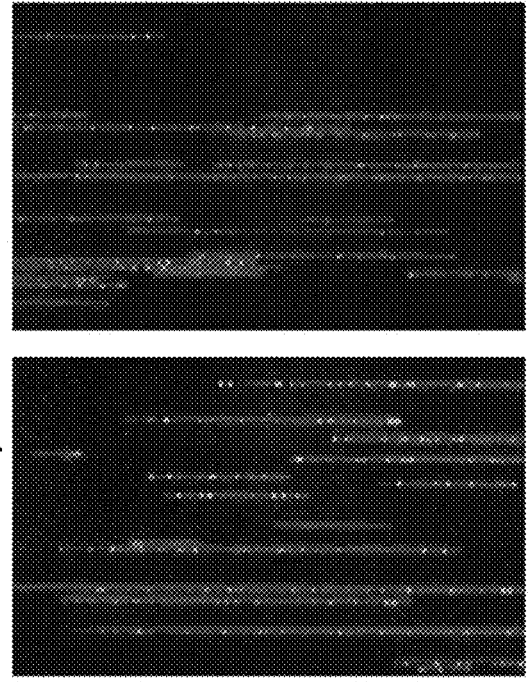
Figure 5B:
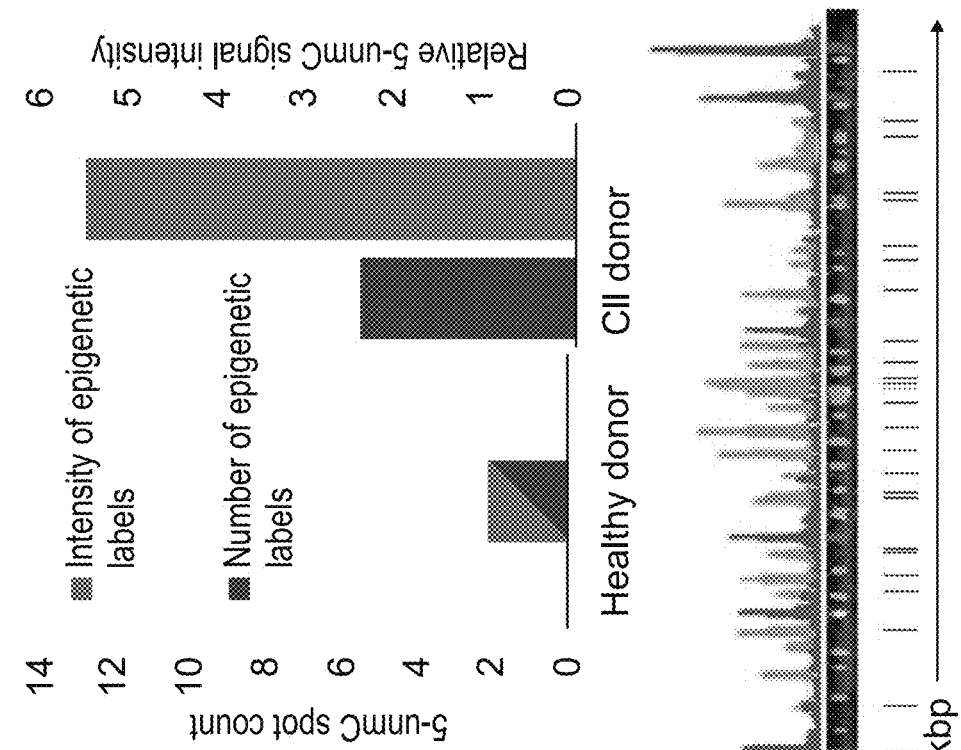
Figure 5C:
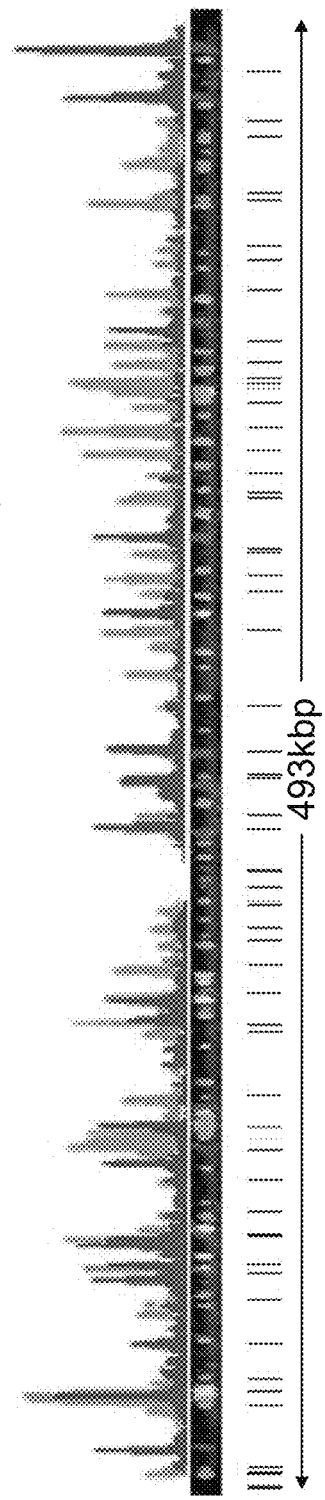

FIGS. 5A-C. DNA epigenetic mapping of human peripheral blood mononuclear cell (PBMC) from a healthy and CLL patient donor. A. representative field of view of stretched DNA in nanochannel array chips from both samples: DNA backbone in blue, genetic labels in green and epigenetic labels in red (more red signal denotes less DNA methylation) B. Global quantification of the normalized number of epigenetic labels detected per 100 kbp and the relative fluorescence intensity of red labels. C. A 493 kbp DNA molecule aligned to chromosome 3 by the green genetic labels, reference in blue lines. The epigenetic intensity pattern along the molecule is presented in the red graph.

Figure 6:
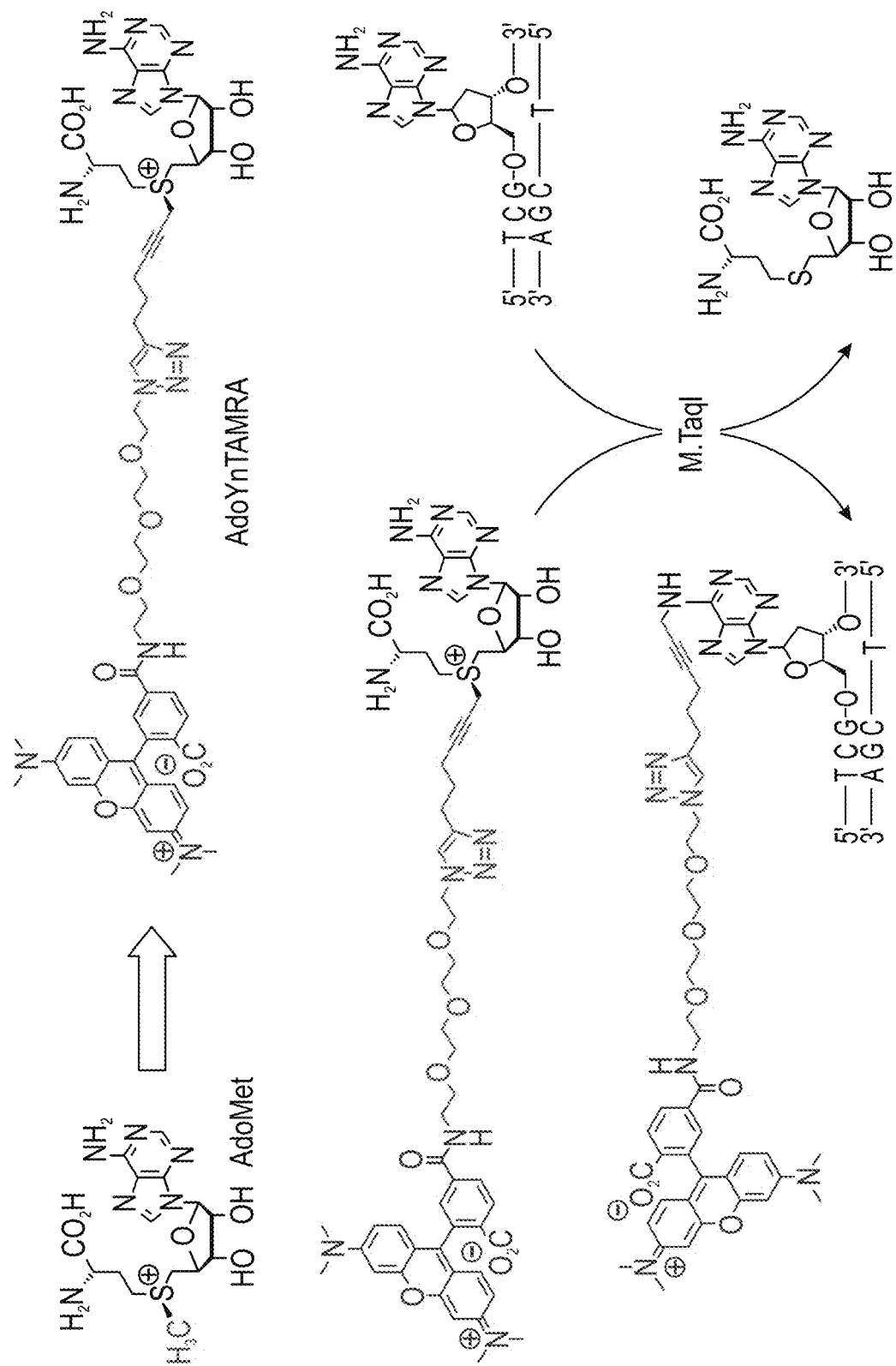

FIG. 6 is an illustration of an exemplary enzymatic reaction that can occur when the CpG site within the TCGA sequence is not methylated using the methyltransferase M.TaqI. The enzyme catalyzes the transfer of the extended side chain from the synthetic cofactor analogue AdoYn-TAMRA to the amino group of adenine with the double-stranded TCGA DNA sequence, leading to fluorescently labeled DNA and the cofactor product S-adenosyl-L-homocystein.

DESCRIPTION OF SPECIFIC EMBODIMENTS OF THE INVENTION

The present invention, in some embodiments thereof, relates to molecular biology and, more particularly, but not exclusively, to simultaneous copy number quantification and DNA methylation detection.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The inventors present a novel concept for genetic and epigenetic profiling of large DNA repeat arrays. Utilizing state-of-the-art optical mapping technology, combined with fluorescence-based methylation detection, they demonstrate automatic, high-throughput analysis of such samples. This approach offers single-molecule level information on the size of the region, the number of repeat units and the methylation status of individual repeats. This detailed information is inaccessible via current research tools such as NGS, DNA arrays and quantitative PCR, which mostly provide averaged data and cannot specifically address individual repeat units.

The present inventors demonstrate the utility of this concept for the D4Z4 repeat array, which is a striking example of how the size and the methylation status of DNA repeats affect disease manifestation. Specifically, the reported approach can distinguish between healthy individuals, FSHD1 and FSHD2 carriers by combining copy number and methylation level information. Moreover, the detailed view of the methylation status of individual repeats may offer new insights regarding the mechanism of disease and may lead to personalized treatment. Notably, the dual-barcode concept is not limited to D4Z4 repeats and various labeling enzymes may be used to address different target sequences, thereby extending the repertoire of available targets for this method.

In addition, optical genome mapping has recently been used to map whole human genomes at high coverage and to highlight genetic variability between individuals with unprecedented detail. This work adds an epigenetic component to optical maps, providing, for the first time, correlated genetic/epigenetic profiles for individual DNA molecules spanning hundreds of thousands of bases. Further development of this technique may serve to map single-molecule methylation patterns on a genome-wide scale, potentially allowing simultaneous genetic/epigenetic haplotyping, as well as ultra-sensitive detection of epigenetic transformations.

Thus, according to a first aspect of the present invention there is provided a method of analyzing the methylation status of a CpG site along a DNA molecule comprising:

(a) contacting the DNA with a methyltransferase enzyme in the presence of a co-factor which is labeled with a detectable moiety under conditions which brings about transfer of the detectable moiety from the co-factor to the DNA;

(b) extending the DNA molecule; and (c) detecting the detectable moiety, wherein the presence of the detectable moiety is indicative of a non-methylated CpG site.

As used herein, the term "methyltransferase enzyme, MTase" refers to an enzyme which transfers the activated methyl group from the natural cofactor S-adenosyl-L-methionine (AdoMet or SAM) to adenine-N6, cytosine-N4 or cytosine-C5 within specific double-stranded DNA sequences ranging from two to eight base pairs.

Preferably, the DNA methyltransferase is an enzyme capable of methylating DNA. More preferably, the methyltransferase is a DNA cytosine-C5 methyltransferase that uses a covalent activation mechanism for the transfer of the methyl group on the C5 position of a target cytosine residue.

Even more preferably, the methyltransferase is a CpG methylation-sensitive MTase, i.e. only recognizes the non-methylated C base in the context of a CpG site (i.e. a region of DNA where a cytosine nucleotide is followed by a guanine nucleotide in the linear sequence of bases along its 5'→3' direction).

In one embodiment, the CpG-methylation sensitive MTase is selected from the group consisting of M.TaqI, M.HhaI, M.HpaII, M.MspI, M.SssI and M.MpeI or a functional derivative thereof.

As used herein the term "DNA" refers to double stranded DNA. The DNA can be a mammalian DNA (e.g., human) or plant DNA in which CpG modifications typically occur or a synthetic DNA in which CpG modifications may be artificially added.

According to an embodiment of the invention, the DNA molecule is a complementary polynucleotide sequence (cDNA) to which CpG modifications have been artificially added, a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

The length of the DNA molecule may vary. Exemplary ranges include, but are not limited to 1-15,000 Kbp, reflecting at the high range the size of a human chromosomes (or chromatin).

According to some embodiments of the invention, the DNA molecule is longer than 20 Kbp.

According to some embodiments of the invention, the DNA molecule is longer than 30 Kbp.

According to some embodiments of the invention, the DNA molecule is longer than 40 Kbp.

According to a particular embodiment, the DNA molecule comprises at least one D4Z4 repeat as set forth in SEQ ID NO: 1.

The co-factor of this aspect of the present invention refers to a small molecular weight AdoMet analogue that contain extended unsaturated side chains instead of a methyl group at the sulfonium center.

The extended side chain, which replaces the methyl group in AdoMet, reduces the reaction rate of the transfer by the MTase due to unfavorable steric effects within the transition state. Therefore, in order to accelerate the reaction rate, a double or triple bond may be placed within the transferred chain, next to the reactive carbon atom, which will lead to stabilization of the transition state and hence to a faster reaction rate.

According to a particular embodiment, the co-factor is S-adenosyl-L-methionine or a derivative thereof.

According to another embodiment, the co-factor is an aziridine co-factor.

According to still another embodiment, the aziridine co-factor is N-adenosylaziridine or 7-deazaadenosylaziridine or a derivative thereof.

According to still another embodiment, the co-factor is a double-activated S-adenosyl-L-methionine or analogue thereof.

The co-factor described herein is preferably attached to a detectable moiety such as a fluorescent moiety, a radioactive moiety, a magnetic moiety, a chromophore, a bioluminescent moiety, a chemiluminescent moiety, a phosphorescent moiety and a heavy metal cluster, as well as any other known detectable moieties.

Thus, for example, in one embodiment, the co-factor is AdoYnTAMRA, AdoYnAtto532 or AdoYnCF640R.

Further examples and descriptions of detectable moieties are provided herein. In some embodiments, the detectable moiety is an agent that is detectable by spectrophotometric measurements, and/or which can be utilized to produce optical imaging. Such agents include, for example, chromophores, fluorescent agents, phosphorescent agents, and heavy metal clusters.

As used herein, the term "chromophore" refers to a chemical moiety that, when attached to another molecule, renders the latter colored and thus visible when various spectrophotometric measurements are applied.

The phrase "fluorescent moiety" refers to a compound that emits light at a specific wavelength during exposure to radiation from an external source.

The phrase "phosphorescent moiety" refers to a compound emitting light without appreciable heat or external excitation as by slow oxidation of phosphorous.

A heavy metal cluster can be for example a cluster of gold atoms used, for example, for labeling in electron microscopy techniques (e.g., AFM).

The term "bioluminescent moiety" describes a substance which emits light by a biochemical process.

The term "chemiluminescent moiety" describes a substance which emits light as the result of a chemical reaction.

According to some embodiments of the invention, the detectable moiety is a fluorescent moiety.

A fluorescent agent can be a protein, quantum dots or small molecules. Common dye families include, but are not limited to Xanthene derivatives: fluorescein, rhodamine, Oregon green, eosin, Texas red etc.; Cyanine derivatives: cyanine, indocarbocyanine, oxacarbocyanine, thiacarbocyanine and merocyanine; Naphthalene derivatives (dansyl and prodan derivatives); Coumarin derivatives; oxadiazole derivatives: pyridyloxazole, nitrobenzoxadiazole and benzoxadiazole; Pyrene derivatives: cascade blue etc.; BODIPY (Invitrogen); Oxazine derivatives: Nile red, Nile blue, cresyl violet, oxazine 170 etc.; Acridine derivatives: proflavin, acridine orange, acridine yellow etc.; Arylmethine derivatives: auramine, crystal violet, malachite green; CF dye (Biotium); Alexa Fluor (Invitrogen); Atto and Tracy (Sigma Aldrich); FluoProbes (Interchim); Tetrapyrrole derivatives: porphin, phtalocyanine, bilirubin; cascade yellow; azure B; acridine orange; DAPI; Hoechst 33258; lucifer yellow; piroxicam; quinine and anthraqinone; squarylium; oligophenylenes; and the like.

Other fluorophores include: Hydroxycoumarin; Aminocoumarin; Methoxycoumarin; Cascade Blue; Pacific Blue; Pacific Orange; Lucifer yellow; NBD; R-Phycoerythrin (PE); PE-Cy5 conjugates; PE-Cy7 conjugates; Red 613; PerCP; TruRed; FluorX; Fluorescein; BODIPY-FL; TRITC; X-Rhodamine; Lissamine Rhodamine B; Texas Red; Aliaphycocyanin; APC-Cy7 conjugates.

Alexa Fluor dyes (Molecular Probes) include: Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, and Alexa Fluor 790.

Cy Dyes (GE Heathcare) include Cyt, Cy3, Cy3B, Cy3.5, Cy5, Cy5.5 and Cy7. Nucleic acid probes include Hoechst 33342, DAPI, Hoechst 33258, SYTOX Blue, ChromomycinA3, Mithramycin, YOYO-1, Ethidium Bromide, Acridine Orange, SYTOX Green, TOTO-1, TO-PRO-1, TO-PRO: Cyanine Monomer, Thiazole Orange, Propidium Iodide (PI), LDS 751, 7-AAD, SYTOX Orange, TOTO-3, TO-PRO-3, and DRAQ5.

Cell function probes include Indo-1, Fluo-3, DCFH, DHR, SNARF.

Fluorescent proteins include Y66H, Y66F, EBFP, EBFP2, Azurite, GFPuv, T-Sapphire, Cerulean, mCFP, ECFP, CyPet, Y66W, mKeima-Red, TagCFP, AmCyan1, mTFP1, S65A, Midoriishi Cyan, Wild Type GFP, S65C, TurboGFP, TagGFP, S65L, Emerald, S65T (Invitrogen), EGFP (Ciontech), Azami Green (MBL), ZsGreen1 (Clontech), TagYFP (Evrogen), EYFP (Clontech), Topaz, Venus, mCitrine, YPet, Turbo YFP, ZsYellow 1 (Clontech), Kusabira Orange (MBL), mOrange, mKO, TurboRFP (Evrogen), tdTomato, TagRFP (Evrogen), DsRed (Clontech), DsRed2 (Clontech), mStrawberry, TurboFP602 (Evrogen), AsRed2 (Clontech), mRFP1, J-Red, mCherry, HcRed1 (Clontech), Katusha, Kate (Evrogen), TurboFP635 (Evrogen), mPlum, and mRaspberry.

Exemplary fluorescent agents include, but are not limited to, Alexa fluor dyes, Cy dyes, Atto dyes, TAMRA dyes, etc., such as, for example, described in the Examples section that follows.

As mentioned, the method of the present invention comprises contacting the DNA with a methyltransferase enzyme in the presence of a co-factor which is labeled with a detectable moiety under conditions which brings about transfer of the detectable moiety from the co-factor to the DNA. An illustration of an exemplary reaction is shown in FIG. 6.

The pH, temperature and time of the reaction may be selected to optimize the transfer of the detectable moiety from the co-factor to the DNA. Thus, for example, the reaction may be carried out at a pH of about 7-8.5, at a temperature of about 50-70° C. for 20 minutes to about 2 hours. Proteinase K may optionally be used following the reaction to disassemble protein-DNA aggregates.

According to some embodiments of the invention, analyzing CpG methylation content is done without subjecting the DNA molecule to fragmentation.

It will be appreciated that the method of this aspect of the present invention further contemplates attaching to the DNA molecule an additional detectable moiety which labels a sequence of the DNA which is not a CpG site using a DNA labeling agent.

In one embodiment, the sequence which is labeled is a repeat sequence, i.e. one which is repeated at least two times, three times, four times, five times, six times, seven times, eight times, nine times, or at least ten times within the length of the DNA. In one embodiment, the sequence is repeated in tandem (i.e. the repetitions are directly adjacent to one another). In another embodiment, the repeat sequence is scattered throughout the DNA molecule.

According to one embodiment, the sequence specific DNA labeling agent is a nicking enzyme.

In one embodiment, the nicking enzyme cuts one strand of a double-stranded DNA at a restriction site.

Exemplary nicking enzymes contemplated by the present invention include, but are not limited to Nb.BsmI, Nb.BvvCI, Nb.BsrDI, Nb.BssSI, Nb.BtsI, Nt.AlwI, Nt.BbvCI, Nt.BsmAI, Nt.BspQI and Nt.BstNBI.

In another embodiment, the nicking enzyme is an enzyme that requires a guide RNA (gRNA) such as Cas9, TALE and ZFN nickase.

ZFNs and TALENs—

Two distinct classes of engineered nucleases, zinc-finger nucleases (ZFNs) and transcription activator-like effector nucleases (TALENs), have both proven to be effective at producing targeted double-stranded breaks.

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is FokI. Additionally FokI has the advantage of requiring dimerization to have nuclease activity and this means the specificity increases dramatically as each nuclease partner recognizes a unique DNA sequence. To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break. Repair of these double-stranded breaks through the nonhomologous end-joining (NHEJ) pathway most often results in small deletions or small sequence insertions. Since each repair made by NHEJ is unique, the use of a single nuclease pair can produce an allelic series with a range of different deletions at the target site. The deletions typically range anywhere from a few base pairs to a few hundred base pairs in length, but larger deletions have successfully been generated in cell culture by using two pairs of nucleases simultaneously (Carlson et al., 2012; Lee et al., 2010). In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs. Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, Calif.).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TALE and TALEN constructs for genome editing applications (can be accessed through www(dot)talendesign (dot)org). TALEN can also be designed and obtained commercially from e.g., Sangamo Biosciences™ (Richmond, Calif.).

CRISPR-Cas System—

Many bacteria and archea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components. The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of Cas9 in conjunction with synthetic gRNAs can be used to produce targeted double-stranded brakes in a variety of different species (Cho et al., 2013; Cong et al., 2013; DiCarlo et al., 2013; Hwang et al., 2013a,b; Jinek et al., 2013; Mali et al., 2013).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

Another contemplated DNA labeling agent is a CpG-methylation insensitive DNA MTase. The labeling agent of this aspect of the present invention transfers a label from a co-factor to a site which does not contain a 5'-CG-3' sequence.

An example of such a DNA MTase is DNA adenine methylase (Dam), such as for example M.EcoDam or derivatives thereof.

M.BseCI is also contermplated as it is not CpG methylation sensitive but recognizes ATCGAT which contains a CpG site.

The detectable moiety which is used to label the DNA according to this embodiment may be identical to the detectable moiety used to label the CpG site. Alternatively, the detectable moiety which is used to label the DNA according to this embodiment may be non-identical to the detectable moiety used to label the CpG site.

In one embodiment, when the detectable moiety used to label the CpG site uses a particular illumination type (e.g. fluorescence), then the detectable moiety used to label the other non-CpG site uses the same illumination type (e.g. fluorescence, but of a different wavelength to the fluorescent moiety used to label the CpG site).

According to a particular embodiment, the detectable moiety is attached to a nucleotide which is incorporated into the sequence following the nicking.

For example, the present inventors contemplate using fluorescent nucleotides such as described in the Examples section herein below.

Prior to, or following step (a) of the method (including or not including the additional labeling reaction), the DNA is extended. According to some embodiments of the invention, the extending is linearly extending.

According to some embodiments of the invention, the extending is effected by depositing the DNA molecule on a surface or extending the DNA molecule in a nanochannel.

As used herein "extended DNA molecule" or "elongated DNA molecule" which is interchangeably used herein refers to a single or plurality elongated and fixed (i.e., immobilized) DNA.

According to some embodiments of the invention, the extended DNA molecules are elongated and fixed in a controllable manner directly onto a solid, planar surface. According to a specific embodiment, this solid, planar surface contains a positive charge density which has been controllably modified such that the single nucleic acid molecules will exhibit an optimal balance between the critical parameters of nucleic acid elongation state, degree of relaxation stability and biological activity. Further, methods, compositions and assays are described by which such an optimal balance can precisely and reproducibly be achieved.

According to alternative or additional embodiments, the single nucleic acid molecules are elongated via flow-based techniques. In such an embodiment, a single nucleic acid molecule is elongated, manipulated (via, for example, a regio-specific restriction digestion), and/or analyzed in a laminar flow elongation device. Such a laminar flow elongation devices and methods of elongating or extending DNA are described in U.S. Patent Application 20030124611, which is hereby incorporated by reference in its entirety.

The elongated, individual labeled DNA molecules can then be utilized in a variety of ways which have applications for the analysis of nucleic acid at the genome level. For example, such nucleic acid molecules may be used to generate ordered, high resolution single nucleic acid molecule restriction maps. This method is referred to herein as "optical mapping" or "optical restriction mapping". Additionally, methods are presented whereby specific nucleotide sequences present within the elongated nucleic acid molecules can be identified. Such methods are referred to herein as "optical sequencing". The optical mapping and optical sequencing techniques can be used independently or in combination on the same individual nucleic acid molecules.

Additionally, methods are also presented for the imaging and sizing of the elongated single nucleic acid molecules. These imaging techniques may, for example, include the use of fluorochromes, microscopy and/or image processing computer software and hardware.

Further description of DNA extension is provided in the Examples section which follows.

The method can be carried out for diagnosing diseases which are associated with an altered methylation status. Such diseases include facioscapulohumeral muscular dystrophy (FSHD) and cancers.

Thus, according to another aspect of the present invention there is provided a method of diagnosing a disease associated with a DNA repeat sequence comprising:

(a) determining the number of repeats of a DNA sequence in DNA molecules of a sample of the subject; and (b) determining the CpG methylation status of the DNA molecules, wherein the number of repeats of the DNA sequence and the CpG methylation status of the DNA molecules is indicative of the disease.

As used herein the term "diagnosing" refers to determining presence or absence of a pathology (e.g., a disease, disorder, condition or syndrome), classifying a pathology or a symptom, determining a severity of the pathology, monitoring pathology progression, forecasting an outcome of a pathology and/or prospects of recovery and screening of a subject for a specific disease.

According to some embodiments of the invention, screening of the subject for a specific disease is followed by substantiation of the screen results using gold standard methods.

Diseases which are associated with DNA repeat sequences include cancer, polyglutamine diseases and FSHD.

Examples of polyglutamine disease which can be diagnosed according to this aspect of the present invention include, but are not limited to Spinocerebellar ataxia Type 3, Dentatorubropallidoluysian atrophy (DRPLA), Huntington's disease (HD), Spinocerebellar ataxia Type 1, Spinocerebellar ataxia Type 2, Spinocerebellar ataxia Type 6, Spinocerebellar ataxia Type 7 and Spinocerebellar ataxia Type 17.

Examples of cancer which can be diagnosed are summarized herein below.

Cancer

Examples of cancers that may be diagnosed using the methods described herein include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; triple negative breast cancer, Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; osteocarcinoma, ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

According to a particular embodiment, the cancer is leukemia (e.g. chronic lymphocytic leukemia).

Detection of the labeled DNA molecule can be done at the single molecule level using optical imaging as further described herein below. Alternatively, detection of labeled DNA molecules can be done at the global level, analyzing the presence or level of CpG modification of a plurality of DNA molecules at the cell, tissue and organism level.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non-limiting fashion. Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Next Generation Sequencing and Sequencing Data Analysis

Purified BAC DNA was sheared using Covaris AFA (Covaris Inc. Woburn Mass., USA) and the fragments were size-separated by electrophoresis using agarose gel, allowing selective extraction of fragments within the range of 150-300 bp. DNA fragments were then adapted to Illumina sequencing using NEXTFlex kit (Bioo Scientific Corporation, Austin Tex., USA) and sequenced using Miseq (Illumina Inc. San Diego, Calif. USA) to a paired-end coverage of 15,000×. Sequencing reads were de-novo assembled using CLC Workbench software (CLC Bio-Qiagen, Aarhus, Denmark). In order to create a coverage map, reads were mapped against a reference sequence, generated from the de-novo assembly contig (which was modified to contain a single D4Z4 repeat), using Bowtie 2 (single-end alignment with an overall alignment rate of 94.56%)[48]. A coverage map of the aligned reads was then generated using BEDTool[49].

Sample Preparation and Fluorescent Labeling

E. coli cells containing the CH16-291A23 BAC were cultured overnight in LB containing 12.5 µg/ml chloramphenicol (Sigma-Aldrich, Rehovot, Israel) at 30° C. BAC DNA was specifically purified from the cells using the NucleoBondXtra BAC kit (MACHEREY-NAGEL Inc. Duren, Gremany). Fluorescent, sequence-specific labeling was generated by two orthogonal chemoenzymatic reactions:

1. by using the DNA MTase M.TaqI, which catalyzes the transfer of a carboxytetramethylrhodamine (TAMRA) fluorophore from the synthetic cofactor AdoYnTAMRA onto the adenine residue within its recognition sequence (TCGA)[45,46]; and 2. by a nick-labeling-repair reaction (NLR) that involves (a) the nicking enzyme Nb.BsmI which generates single-strand nicks at its specific recognition sites (GAATGC), (b) a DNA polymerase enzyme that incorporates fluorescent nucleotides at the nicked sites and finally, (c) a DNA ligase enzyme to repair the single-strand breaks at the nicked sites.

For the NLR reaction, 900 ng of DNA was firstly reacted with 30 units of Nb.BsmI (New England Biolabs Inc., Ipswich Mass., USA) in a buffer (NEB buffer 3.1), in a total reaction volume of 30 µl for 120 minutes at 65° C. Next, the DNA was reacted with 15 units of Taq DNA polymerase (New England Biolabs Inc., Ipswich Mass., USA) in the presence of the following nucleotides: dGTP, dCTP dATP (Sigma-Aldrich, Rehovot, Israel) and the fluorescent nucleotide dUTP-Atto647 (Jena Bioscience GmbH, Jena, Germany) in a final concentration of 600 nM (each). The reaction was carried out in a reaction buffer (Thermoplol buffer, New England Biolabs Inc., Ipswich Mass., USA) at a total volume of 45 μl for 60 minutes at 72° C. Finally, the DNA was reacted with 120 units of Taq DNA ligase (New England Biolabs Inc., Ipswich Mass., USA) in 0.5 mM NAD (New England Biolabs Inc., Ipswich Mass., USA), in a reaction buffer (Thermoplol buffer, New England Biolabs Inc., Ipswich Mass., USA), in the presence of 10 μM dNTP mix, in a total reaction volume of 60 μL for 30 minutes at 45° C.

The M.TaqI labeling reaction was carried out as follows: 1 μg of DNA was reacted with 37.5 ng of M.TaqI and 40 μM of AdoYnTAMRA in labeling buffer (20 mM Tris-HOAc, 10 mM Mg(Cl)2, 50 mM KOAc, 1 mM DTT, pH 7.9) in the presence of 0.01% Triton-X 100 and 0.1 mg/ml BSA in a total reaction volume of 25 μL at 60° C. for 1 hour (FIG. 4A). The labeled DNA was reacted with 40 ng of protein kinase K (Sigma-Aldrich, Rehovot, Israel) at 45° C. for 1 hour to disassemble protein-DNA aggregates.

In the dual labeling experiments, DNA was initially labeled with Nb.BsmI (the NLR reaction described above) and then 0.05 μg-0.5 μg of the labeled DNA was reacted with M.TaqI as described above (the reaction was scaled down accordingly). Post labeling, all reactions were cleaned by ethanol precipitation as has been described previously[46]. CpG methylation of the BAC DNA was performed prior to labeling using the CpG methyltransferase M.SssI (Thermo Scientific, Waltham, Mass., USA) in recommended conditions. For the fully methylated samples, the amount of enzyme used was twice that suggested by the supplier, to ensure complete methylation. Methylation was verified by digestion with a CpG methylation-sensitive restriction enzyme (R.HpaII, New England Biolabs Inc., Ipswich Mass., USA), followed by electrophoreses to ensure that the DNA was protected (data not shown).

To obtain partial methylation, the reaction was carried out using the recommended amount of enzyme, but for 75% of the recommended incubation time. Prior to imaging, the labeled DNA was stained with 0.5 μM of YOYO-1 (Invitrogen, Carlsbad, Calif., USA) for visualization of its contour.

DNA Stretching and Imaging

To stretch the DNA from its coiled conformation into a linear form, allowing imaging of its contour, two types of experimental schemes were used:

1. The first type of stretch used modified glass surfaces. In this approach, DNA samples are flowed, by applying capillary forces or using microfluidics, on glass surfaces that are chemically modified to facilitate the DNA's anchoring and stretching on the surfaces. To demonstrate the versatility of the method, three common variants of modified glass were analyzed. DNA was stretched and data was collected from all of them:
   a. In the first method, DNA was flowed by capillary forces on glass surfaces activated with an acid mixture and coated with positive and hydrophobic silanes[29].
   b. In the second method, glass coated with the hydrophobic polymer Zeonex[50] was used.
   c. The third method involved the hydrophobic cover-glass commercially available from Genomic Vision (Genomic Vision, Bagneux, France).

After stretching, the DNA was imaged using an epifluorescence microscope (FEI Munich GmbH, Germany) equipped with a high-resolution EMCCD IXon888 camera (Andor Technology Ltd, Belfast, UK). A 150 W Xenon lamp (FEI Munich GmbH, Germany) was used for excitation with filter sets of 485/20ex and 525/30em, 560/25ex and 607/36em, and 650/13ex and 684/24em (Semrock Inc., Rochester N.Y., USA) for the YOYO-1, TAMRA, and Atto-647 channels accordingly.

2. The second type of stretching was applied by forcing the DNA into nanochannels using an electric field. This was carried out using the Irys instrument (BioNanoGenomics Inc., San Diego Calif., USA). An Irys set includes: a disposable chip containing a silicone fabricated array of nanochannels (~45 nm square cross section), a voltaic device that induces an electric field to drive the DNA into the nanochannels (forcing it to stretch along them) and a motorized, triple-color fluorescent microscope to image the stretched DNA[42].

Read Depth Analysis

To estimate the number of repeats in the BAC, based on the raw sequencing data, a computational method called read depth analysis was applied. This type of analysis estimates the copy number of a certain repeat along the sequenced DNA from the relative number of times that it is represented in the output sequencing data. It is based on the assumption that all bases in the sequence were sequenced to the same extent. Thus, if a certain region is represented N times more than other regions in the sequencing read data, it indicates that this region is also N times more abundant in the studied DNA.

The analysis was based on the raw short reads obtained from sequencing. As a reference sequence, to which the reads were aligned, the contig produced by de-novo assembly was used. This model contig represents the BAC's sequence assuming a single repeat. Higher read depth along the repeat sequence, compared to the non-repetitive sequence, would indicate a greater number of repeats in the actual BAC.

Data Analysis

The DNA that was stretched on the modified glass surfaces was manually aligned, according to the barcode created by the labels on its non-repetitive region. This enabled detection of the starting point of the repeat array, allowing counting of individual repeat units. Raw data of labeled DNA that were imaged with the Irys device were detected and digitized by custom image-processing and analysis software (IrysView[37]). Subsequently, the detected DNA molecules were either aligned to a reference sequence, based on the expected and detected label positions, or de-novo assembled into an experimental barcode or contig that could then be compared with the theoretical barcode.

To generate plots of labeling intensity along the BAC sequence (FIG. 4C), the specific bp location of each M.TaqI label was used. Each molecule was first anchored to the reference according to the alignment results in the Nb.BsmI channel (IrysView) and the M.TaqI positions were then extracted by extrapolation (in-house software). The total number of M.TaqI labels were then counted at each genomic position using BEDTools[49], as well as the total number of molecules aligned to each position. A score for each genomic position was calculated by dividing the total number of labels by the total number of aligned molecules (simply, a score of 1 would mean that all the molecules overlapping this bp had a label on this bp, while 0 would mean that none of the molecules had such a label). This value was then normalized according to the minimum and maximum values of the entire data. Prior to counting the total number of labels, we expanded each label to cover a 1 kbp region (i.e., we assumed that the label covered 500 bp upstream and 500 bp downstream from the precise location it was fitted to). This was done in order to bridge a gap between the digital detection and the actual data: due to diffraction limits, each single label generates a Gaussian shaped spot, typically with a full width at half maximum of 1 stretched kpb. The detection software, on the other hand, usually attributes the label's location to the center of the Gaussian (where it is most likely to actually be).

Example 1

Quantification of DNA Tandem Repeats is Inaccessible to NGS

The present inventors first attempted to evaluate the copy number of the studied array by NGS depth analysis[40]. They reasoned that the number of reads representing the repeat unit, relative to the number of reads detected for a single copy region, would provide the array copy number. Purified BAC DNA was sequenced using Illumina MiSeq to a read depth of 15,000×. De-novo assembly of the sequencing reads resulted in one major 51-kbp long contig. The contig did not include a whole D4Z4 repeat and was almost entirely composed of the non-repetitive sequence of the BAC (the pTARBAC6 cloning vector and a 39-kbp long genomic region that lies adjacent to the D4Z4 repeats on chromosome 4). The contig sequence was in 99.8% agreement (BLAT analysis[41]) with the known human sequence and we used read depth analysis to assess the D4Z4 copy number. Briefly, all sequencing reads were aligned to the BAC's reference sequence, containing only one repeat, and the copy number was calculated as the ratio between the number of reads ("coverage") aligned to the repetitive and the non-repetitive regions respectively. The coverage along the non-repetitive sequence displayed variation of up to 25%, while the coverage along the repeat sequence was extremely variable, averaging 60% of the mean read depth (FIG. 1C). The ratio between the median coverage value along the repetitive and non-repetitive sequences was ~8, implying that this is the number of D4Z4 repeats along the BAC (FIG. 1D). However, the large standard deviation values strongly demonstrate the unreliability of this method, as well as the sensitivity of PCR amplification and NGS to the exact content of the investigated sequence.

Example 2

Optical Mapping Allows Direct and Precise Quantification of DNA Repeats, with Single-Repeat and Single-Molecule Resolution Next, the present inventors attempted to directly visualize the repeats along stretched DNA molecules. They reasoned that tailored labeling of specific sequence motifs would highlight individual repeats and allow physical counting of the copy number. Sequence-specific nicking enzymes were used to create a distinct pattern of nicks along the BAC DNA. The nicks were then healed with fluorescent nucleotides to create a genetic fluorescent barcode[42]. It was found that by using the nicking enzyme Nb.BsmI, a distinct fluorescent barcode could be generated along the D4Z4 repeat array (FIG. 2A). This enzyme has a single recognition site (GAATGC) on every D4Z4 repeat sequence, yielding a single distinct fluorescent tag for each repeat unit. The labeled DNA was stretched for visualization on modified glass surfaces, using a simple micro fluidic scheme. This method allowed fluorescent imaging of the entire DNA contour and localization of individual fluorescent labels along the DNA (FIG. 2A). The stretched BAC molecules exhibited a characteristic fluorescent pattern, which could be divided into two types. The first spanned the non-repetitive region, where fluorescent labels exhibited a unique fluorescence "barcode" according to the underlying sequence[42] (this region, on both ends of the displayed molecules, is highlighted in grey on FIGS. 2A-B). The second type spanned the repetitive region, where individual labels were equally spaced allowing direct quantification of the repeats. Fluorescence profiles extracted from the images of the stretched DNA molecules were clustered and aligned to each other based on the sequence-specific barcode characterizing the non-repetitive region. Following alignment, repeats were counted on multiple intact molecules, unambiguously establishing the exact number of D4Z4 units on this BAC to be 23 (images of 3 molecules are shown in FIG. 2A).

The present inventors next checked whether this labeling and detection paradigm could be applied in an automated and robust manner, using commercially available technology. The same sample was analyzed on an Irys instrument (BioNanoGenomics Inc., CA. USA), which facilitates high-throughput DNA stretching and imaging in nanochannel array chips. For high throughput, the sample was repeatedly driven into the nanochannels using an electric field and flushed out after imaging (FIG. 2B). The post-imaging analysis, performed by the Irys software suit, involved automatic label detection and de-novo assembly of the molecules into a continuous consensus barcode. The resulting consensus was created in an unsupervised manner based on label patterns from approximately one thousand detected molecules[43,44]. When comparing the non-repetitive region of this contig to the one predicted from the known sequence, an almost perfect match was obtained (p-value<$10^{-43}$, FIG. 2B). The consensus repetitive region was composed of 23 repeats, confirming the manual analysis performed on the surface-immobilized DNA sample. The fact that both independent detection schemes resulted in an identical value for the number of D4Z4 repeats demonstrates the applicability of this approach for determining copy number in the pathogenic D4Z4 region.

Example 3

CpG DNA Methylation can be Detected at the Single-Molecule Level by DNA-Methyltransferase Assisted Labeling Since DNA methylation at D4Z4 repeats plays a crucial role in the manifestation of disease, the present inventors focused on the ability to independently assess the methylation status of the region. This involved an orthogonal method for sequence-specific labeling of DNA, by manipulating methyltransferase enzymes (MTases) to perform the labeling reaction. It has recently been demonstrated that the DNA MTase M.TaqI (with the TCGA recognition site) may be "tricked" into directly incorporating a fluorophore onto its recognition site by using synthetic co-factor analogs[46] (FIG. 3A, upper panel). This method was used to generate DNA barcodes for optical mapping[46] and is ideally suited for labeling the D4Z4 repeats with two proximal labels on each repeat unit (FIG. 3A, lower panel).

Here it has been demonstrated that M.TaqI labeling is CpG methylation sensitive, i.e., if the CpG that lies in the enzyme's recognition site (TCGA) is methylated, the enzyme will not incorporate a fluorophore and no label will be detected (FIG. 3B. upper panel). Thus the labeling pattern resulting from M.TaqI labeling can indicate the methylation status of the studied DNA, and if used in combination with another mapping technique, can reveal the methylation status of specific genomic locations. Since not only the number of D4Z4 repeats is relevant to the nature of FSHD but also their methylation status[23], the present inventors applied both M.TaqI and Nb.BsmI labeling to the FSHD model DNA, for simultaneous copy number and methylation analysis. They used red fluorophores for genetic mapping and green fluorophores for methylation detection on both native, unmethylated BAC DNA and on methylated BAC DNA in which all the CpGs were pre-methylated using the CpG methyltransferase M.SssI (New England Biolabs Inc., Ipswich Mass., USA). As expected, the unmethylated DNA was dually labeled by both enzymes and thus contained two layers of barcode (in red and in green), in agreement with the theoretical dual-color barcode (FIG. 3A). The methylated DNA, on the other hand, exhibited fluorescent labels only in the red channel, indicating that M.TaqI sites were blocked by methylation (FIG. 3B).

Example 4

Optical Mapping Enables High-Throughput, Automatic Detection of Variable Methylation Levels at Single-Repeat Resolution To simulate the native state, where repeat arrays are methylated to variable levels, DNA was partially methylated using the CpG methyltransferase M.SssI. The dual labeling reaction was repeated on the partially methylated sample, as well as on an unmethylated control, and both were run on the Irys instrument (BioNanoGenomics Inc., CA. USA). A three-laser protocol was utilized to allow excitation of the DNA contour with blue, the methylation barcode with green and the genetic barcode with red. After image analysis, the red Nb.BsmI labels were used for automated de-novo assembly and the consensus map with the 23 repeats was generated as described earlier (and depicted in FIG. 2B). With thousands of molecules now aligned to the consensus map, the green methylation patterns generated by M.TaqI on the unmethylated and partially methylated samples could be compared.

Examining the imaged fluorescent methylation barcodes along three unmethylated molecules, it is clear that they are in agreement with the theoretical barcode for M.TaqI along the BAC (FIG. 4A). The unmethylated sample shows frequent labeling, at the expected locations. To compare the unmethylated with a partially methylated sample, and to illustrate how sampling large amounts of genomic data can contribute to understanding the region's genetics and epigenetics, two plots of integrated label counts were generated (FIGS. 4B and 4C) based on all the molecules detected in each data set (18074 unmethylated DNA molecules and 9089 partially methylated molecules). The amount of labeling on the unmethylated BAC was significantly higher than that along the partially methylated BAC (p-value<$10^{-50}$, t-test). These results clearly demonstrate that this dual labeling scheme enables not only single-molecule and single-repeat resolution but also assessment of the average methylation status for each individual repeat in the array across a population of different DNA molecules.

Example 5

Analysis of Methylation Status of DNA from Cancer Cells

The genome-wide methylation profile of PBMCs from a patient diagnosed with chronic lymphocytic leukemia (cll) and a healthy donor were mapped. DNA was fluorescently labeled at unmethylated CpG by the CpG-specific DNA cytosine-C5 methyltransferase M.SssI (Q142A/N370A). The methyltransferase was fed with a modified cofactor (AdoYnAzide), followed by covalent attachment of a fluorophore to specifically label all unmethylaed CpG sites (red).

The relative global methylation level was measured by comparing the number of epigenetic spots along the DNA for each sample or by summing the overall red intensity along the DNA in both samples (FIG. 5B). The latter allows overcoming optical resolution because close-by methylation sites that cannot be resolved by imaging will still display a stronger fluorescence intensity. In this case, it is clear that cancer cells show global reduction in methylation levels (more red signal along the DNA) and that measuring the intensity revealed a much more dramatic methylation reduction compared to counting the number of spots.

Mapping of methylation profiles to the genome was achieved by labeling the DNA with a second color (green), at specific sequence motives using nick translation, with the nicking enzyme Nt.BspQI so as to align the DNA molecules to the reference human genome (FIG. 5C). The labeled DNA was stretched and imaged on nanochannel array chips and the fluorescence intensity from the epigenetic labels was detected and analyzed (FIG. 5A).

REFERENCES

Other References are Provided in the Document (1) Schmid, C. W. Organization of the Human Genome Transcription. 345-358.
(2) Batzer, M. a; Deininger, P. L. Alu Repeats and Human Genomic Diversity. *Nat. Rev. Genet.* 2002, 3, 370-379.
(3) Treangen, T. J.; Salzberg, S. L. Repetitive DNA and next-Generation Sequencing: Computational Challenges and Solutions. *Nat. Rev. Genet.* 2012, 13, 36-46.
(4) Mather, K. A.; Jorm, A. F.; Parslow, R. A.; Christensen, H. Is Telomere Length a Biomarker of Aging? A Review. *J. Gerontol. A. Biol. Sci. Med. Sci.* 2011, 66, 202-213.
(5) M. Duyao, C. Ambrose, R. Myers, A. Novelletto, F. Persichetti, M. Frontali, S.
Folstein, C. Ross, M. Franz, M. Abbott, J. Gray, P. Conneally, A. Young, J. Penney, Z. Hollingsworth, I. Shoulson, A. Lazzarini, A. Falek, W. Koroshetz, D. Sax, E. Bird, J. Von, & M. M. Trinucleotide Repeatlength Instability and Age of Onset in Huntington's Disease. *Nat. Genet.* 1993, 4, 387-392.
(6) Maarel, M. Van Der; Deidda, G.; Lemmers, R. J. L. F.; Overveld, P. G. M. Van; Wielen, M. Van Der; Hewitt, J. E.; Sandkuijl, L.; Bakker, B.; Ommen, G. B. Van; Padberg, G. W.; et al. De Novo Facioscapulohumeral Muscular Dystrophy: Frequent Somatic Mosaicism, Sex-Dependent Phenotype, and the Role of Mitotic Transchromosomal Repeat Interaction between Chromosomes 4 and 10. 1996, 4, 26-35.
(7) Edwards, A.; Hammond, H. A.; Jin, L.; Caskey, C. T.; Chakraborty, R. Genetic Variation at Five Trimeric and Tetrameric Tandem Repeat Loci in Four Human Population Groups. *Genomics* 1992, 12, 241-253.
(8) Bird, A. DNA Methylation Patterns and Epigenetic Memory. *Genes Dev.* 2002, 16, 6-21.
(9) Hansen, K. D.; Timp, W.; Bravo, H. C.; Sabunciyan, S.; Langmead, B.; McDonald, O. G.; Wen, B.; Wu, H.; Liu, (9) ...Y.; Diep, D.; et al. Increased Methylation Variation in Epigenetic Domains across Cancer Types. *Nat. Genet.* 2011, 43, 768-775.

(10) Levy-Sakin, M.; Grunwald, A.; Kim, S.; Gassman, N. R.; Gottfried, A.; Antelman, J.; Kim, Y.; Ho, S. O.; Samuel, R.; Michalet, X.; et al. Toward Single-Molecule Optical Mapping of the Epigenome. *ACS Nano* 2014, 8, 14-26.

(11) Osoegawa, K.; Mammoser, A. G.; Wu, C.; Frengen, E.; Zeng, C.; Catanese, J. J.; De Jong, P. J. A Bacterial Artificial Chromosome Library for Sequencing the Complete Human Genome. *Genome Res.* 2001, 11, 483-496.

(12) Houldsworth, J.; Chaganti, R. S. Comparative Genomic Hybridization: An Overview. *Am. J. Pathol.* 1994, 145, 1253-1260.

(13) Nicklas, J. A.; Buel, E. Development of an Alu-Based, Real-Time PCR Method for Quantitation of Human DNA in Forensic Samples*. 2003.

(14) Dheda, K.; Huggett, J. F.; Chang, J. S.; Kim, L. U.; Bustin, S. a; Johnson, M. a; Rook, G. a W.; Zumla, a. The Implications of Using an Inappropriate Reference Gene for Real-Time Reverse Transcription PCR Data Normalization. *Anal. Biochem.* 2005, 344, 141-143.

(15) Korshunova, Y.; Maloney, R. K.; Lakey, N.; Citek, R. W.; Bacher, B.; Budiman, A.; Ordway, J. M.; McCombie, W. R.; Leon, J.; Jeddeloh, J. A.; et al. Massively Parallel Bisulphite Pyrosequencing Reveals the Molecular Complexity of Breast Cancer-Associated Cytosine-Methylation Patterns Obtained from Tissue and Serum DNA. *Genome Res.* 2008, 18, 19-29.

(16) Bock, C.; Tomazou, E. M.; Brinkman, A. B.; Müller, F.; Simmer, F.; Gu, H.; Jager, N.; Gnirke, A.; Stunnenberg, H. G.; Meissner, A. Quantitative Comparison of Genome-Wide DNA Methylation Mapping Technologies. *Nat. Biotechnol.* 2010, 28, 1106-1114.

(17) Cabianca, D. S.; Gabellini, D. The Cell Biology of Disease: FSHD: Copy Number Variations on the Theme of Muscular Dystrophy. *J. Cell Biol.* 2010, 191, 1049-1060.

(19) Lemmers, R. J. L. F.; Vliet, P. J. Van Der; Klooster, R.; Sacconi, S.; Camaño, P.; Dauwerse, J. G.; Snider, L.; Straasheijm, K. R.; Ommen, G. J. Van; Padberg, G. W.; et al. A Unifying Genetic Model for Facioscapulohumeral Muscular Dystrophy. *Science (80-.).* 2010, 1650-1654.

(20) Yao, Z.; Snider, L.; Balog, J.; Lemmers, R. J. L. F.; Van Der Maarel, S. M.; Tawil, R.; Tapscott, S. J. DUX4-Induced Gene Expression Is the Major Molecular Signature in FSHD Skeletal Muscle. *Hum. Mol. Genet.* 2014, 23, 5342-5352.

(21) Gabellini, D.; Green, M. R.; Tupler, R. Inappropriate Gene Activation in FSHD: A Repressor Complex Binds a Chromosomal Repeat Deleted in Dystrophic Muscle. 1998, 339-348.

(22) Lemmers, R. J. L. F.; Tawil, R.; Petek, L. M.; Balog, J.; Block, G. J.; Santen, G. W. E.; Amell, A. M.; van der Vliet, P. J.; Almomani, R.; Straasheijm, K. R.; et al. Digenic Inheritance of an SMCHD1 Mutation and an FSHD-Permissive D4Z4 Allele Causes Facioscapulohumeral Muscular Dystrophy Type 2. *Nat. Genet.* 2012, 44, 1370-1374.

(23) Gaillard, M.-C.; Roche, S.; Dion, C.; Tasmadjian, A.; Bouget, G.; Salort-Campana, E.; Vovan, C.; Chaix, C.; Broucqsault, N.; Morere, J.; et al. Differential DNA Methylation of the D4Z4 Repeat in Patients with FSHD and Asymptomatic Carriers. *Neurology* 2014, 83, 733-742.

(24) Overveld, P. G. M. Van; Lemmers, R. J. F. L.; Deidda, G.; Sandkuijl, L.; Padberg, G. W.; Frants, R. R.; Maarel, S. M. Van Der. Interchromosomal Repeat Array Interactions between Chromosomes 4 and 10: A Model for Subtelomeric Plasticity. 2879-2884.

(25) Zatz, M.; Marie, S. K.; Passos-bueno, M. R.; Vainzof, M.; Campiotto, S.; Cerqueira, A.; Wijmenga, C.; Padberg, G.; Frants, R. High Proportion of New Mutations and Possible Anticipation in Brazilian Facioscapulohumeral Muscular Dystrophy Families. 1993, 99-105.

(26) Tawil, R.; Forrester, J.; Griggs, R. C.; Mendell, J.; Kissel, J.; McDermott, M.; King, W.; Weiffenbach, B.; Figlewicz, D. Evidence for Anticipation and Association of Deletion Size with Severity in Facioscapulohumeral Muscular Dystrophy. The FSH-DY Group. *Ann. Neurol.* 1996, 39, 744-748.

(27) van der Maarel, S. M.; Deidda, G.; Lemmers, R. J.; van Overveld, P. G.; van der Wielen, M.; Hewitt, J. E.; Sandkuijl, L.; Bakker, B.; van Ommen, G. J.; Padberg, G. W.; et al. De Novo Facioscapulohumeral Muscular Dystrophy: Frequent Somatic Mosaicism, Sex-Dependent Phenotype, and the Role of Mitotic Transchromosomal Repeat Interaction between Chromosomes 4 and 10. *Am. J. Hum. Genet.* 2000, 66, 26-35.

(28) Levy-Sakin, M.; Ebenstein, Y. Beyond Sequencing: Optical Mapping of DNA in the Age of Nanotechnology and Nanoscopy. *Curr. Opin. Biotechnol.* 2013, 1-9.

(29) Sidorova, J. M.; Li, N.; Schwartz, D. C.; Folch, A.; Monnat, R. J. Microfluidic-Assisted Analysis of Replicating DNA Molecules. *Nat. Protoc.* 2009, 4, 849-861.

(30) Meng, X.; Benson, K.; Chada, K.; Huff, E. J.; Schwartz, D. C. Optical Mapping of Lambda Bacteriophage Clones Using Restriction Endonucleases. *Nat. Genet.* 1995, 9, 432-438.

(31) Nilsson, A. N.; Emilsson, G.; Nyberg, L. K.; Noble, C.; Stadler, L. S.; Fritzsche, J.; Moore, E. R. B.; Tegenfeldt, J. O.; Ambjornsson, T.; Westerlund, F. Competitive Binding-Based Optical DNA Mapping for Fast Identification of Bacteria—Multi-Ligand Transfer Matrix Theory and Experimental Applications on *Escherichia Coli*. *Nucleic Acids Res.* 2014, 42, e118.

(32) Vranken, C.; Deen, J.; Dirix, L.; Stakenborg, T.; Dehaen, W.; Leen, V.; Hofkens, J.; Neely, R. K. Super-Resolution Optical DNA Mapping via DNA Methyltransferase-Directed Click Chemistry. *Nucleic Acids Res.* 2014, 42, e50.

(33) Nifker, G.; Levy-Sakin, M.; Berkov-Zrihen, Y.; Shahal, T.; Gabrieli, T.; Fridman, M.; Ebenstein, Y. One-Pot Chemoenzymatic Cascade for Labeling of the Epigenetic Marker 5-Hydroxymethylcytosine. *Chembiochem* 2015.

(34) Zirkin, S.; Fishman, S.; Sharim, H.; Michaeli, Y.; Don, J.; Ebenstein, Y. Lighting up Individual DNA Damage Sites by in Vitro Repair Synthesis. *J. Am. Chem. Soc.* 2014, 136, 7771-7776.

(35) Michaeli, Y.; Shahal, T.; Torchinsky, D.; Grunwald, A.; Hoch, R.; Ebenstein, Y. Optical Detection of Epigenetic Marks: Sensitive Quantification and Direct Imaging of Individual Hydroxymethylcytosine Bases. *Chem. Commun. (Camb).* 2013, 49, 8599-8601.

(36) Nguyen, K.; Walrafen, P.; Bernard, R.; Attarian, S.; Chaix, C.; Vovan, C.; Renard, E.; Dufrane, N.; Pouget, J.; Vannier, A.; et al. Molecular Combing Reveals Allelic Combinations in Facioscapulohumeral Dystrophy. *Ann. Neurol.* 2011, 70, 627-633.

(37) Cao, H.; Hastie, A. R.; Cao, D.; Lam, E. T.; Sun, Y.; Huang, H.; Liu, X.; Lin, L.; Andrews, W.; Chan, S.; et al. Rapid Detection of Structural Variation in a Human

(38) Huichalaf, C.; Micheloni, S.; Ferri, G.; Caccia, R.; Gabellini, D. DNA Methylation Analysis of the Macrosatellite Repeat Associated with FSHD Muscular Dystrophy at Single Nucleotide Level. *PLoS One* 2014, 9, e115278.

(39) Mostovoy, Y.; Levy-Sakin, M.; Lam, J.; Lam, E. T.; Hastie, A. R.; Marks, P.; Lee, J.; Chu, C.; Lin, C.; Džakula, .; et al. A Hybrid Approach for de Novo Human Genome Sequence Assembly and Phasing. *Nat. Methods* 2016, 12-17.

(40) Yoon, S.; Xuan, Z.; Makarov, V.; Ye, K.; Sebat, J. Sensitive and Accurate Detection of Copy Number Variants Using Read Depth of Coverage. *Genome Res.* 2009, 19, 1586-1592.

(41) Kent, W. J. BLAT—The BLAST-Like Alignment Tool. 2002, 656-664.

(42) Das, S. K.; Austin, M. D.; Akana, M. C.; Deshpande, P.; Cao, H.; Xiao, M. Single Molecule Linear Analysis of DNA in Nano-Channel Labeled with Sequence Specific Fluorescent Probes. *Nucleic Acids Res.* 2010, 38, e177.

(43) Pendleton, M.; Sebra, R.; Pang, A. W. C.; Ummat, A.; Franzen, O.; Rausch, T.; Stutz, A. M.; Stedman, W.; Anantharaman, T.; Hastie, A.; et al. Assembly and Diploid Architecture of an Individual Human Genome via Single-Molecule Technologies. *Nat. Methods* 2015, 12, 780-786.

(44) Thomas Anantharaman, B. M. False Positives in Genomic Map Assembly and Sequence Validation file:///C:/Users/grunwald/Downloads/FalsePositives.pdf (accessed Mar. 30, 2016).

(45) Hanz, G. M.; Jung, B.; Giesbertz, A.; Juhasz, M.; Weinhold, E. Sequence-Specific Labeling of Nucleic Acids and Proteins with Methyltransferases and Cofactor Analogues. *J. Vis. Exp.* 2014, 93, e52014.

(46) Grunwald, A.; Dahan, M.; Giesbertz, A.; Nilsson, A.; Nyberg, L. K.; Weinhold, E.; Ambjörnsson, T.; Westerlund, F.; Ebenstein, Y. Bacteriophage Strain Typing by Rapid Single Molecule Analysis. *Nucleic Acids Res.* 2015, 43, e117.

(47) Choi, S. H.; Worswick, S.; Byun, H.-M.; Shear, T.; Soussa, J. C.; Wolff, E. M.; Douer, D.; Garcia-Manero, G.; Liang, G.; Yang, A. S. Changes in DNA Methylation of Tandem DNA Repeats Are Different from Interspersed Repeats in Cancer. *Int. J. Cancer* 2009, 125, 723-729.

(48) Langmead, B.; Salzberg, S. L. Fast Gapped-Read Alignment with Bowtie 2. *Nat. Methods* 2012, 9, 357-359.

(49) Quinlan, A. R.; Hall, I. M. BEDTools: A Flexible Suite of Utilities for Comparing Genomic Features. *Bioinformatics* 2010, 26, 841-842.

(50) Deen, J.; Sempels, W.; De Dier, R.; Vermant, J.; Dedecker, P.; Hofkens, J.; Neely, R. K. Combing of Genomic DNA from Droplets Containing Picograms of Material. *ACS Nano* 2015, 9, 809-816.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of diagnosing a disease associated with a DNA repeat sequence comprising:
   (a) determining the number of repeats of a DNA sequence in DNA molecules of a sample of the subject by covalently attaching to the DNA molecules a detectable moiety which labels said repeats of said DNA sequence using i) a sequence-specific CpG-methylation-insensitive DNA methyltransferase (DNA MTase) or ii) a sequence specific nicking enzyme in a nick-labeling-repair (NLR) reaction or both i) and ii); and
   (b) determining the CpG methylation status of said DNA molecules, wherein the number of repeats of said DNA sequence and the CpG methylation status of said DNA molecules is indicative of the disease,
   wherein the number of repeats and the CpG methylation status are determined for the same DNA molecules of said sample by dual labeling.

2. The method of claim 1, wherein step (b) is effected by contacting said DNA molecules with a CpG-methylation-sensitive methyltransferase (MTase) enzyme in the presence of a co-factor which is labeled with a detectable moiety under conditions which brings about transfer of said detectable moiety from said co-factor to said DNA molecules.

3. The method of claim 2, further comprising stretching the DNA molecules following said contacting.

4. The method of claim 3, wherein said stretching is linearly stretching.

5. The method of claim 1, wherein said covalently attaching said detectable moiety is effected using a sequence specific nicking enzyme in said NLR reaction.

6. The method of claim 5, wherein said nicking enzyme is selected from the group consisting of Nb.BsmI, Nb.BvvCI, Nb.BsrDI, Nb.BssSI, Nb.BtsI, Nt.AlwI, Nt.BbvCI, Nt.BsmAI, Nt.BspQI and Nt.BstNBI.

7. The method of claim 5, wherein said nicking enzyme is selected from the group consisting of Cas9, TALE and ZFN nickase.

8. The method of claim 1, wherein said covalently attaching said detectable moiety is effected using a CpG-methylation insensitive DNA methyltransferase (MTase).

9. The method of claim 8, wherein said CpG-methylation insensitive DNA methyltransferase has a double-stranded recognition sequence which does not contain the 5'-CG-3' sequence.

10. The method of claim 9, wherein said CpG-methylation insensitive DNA methyltransferase is a DNA adenine methylase (Dam), M.EcoDam or a derivative thereof or M.BseCI or a derivative thereof.

11. A method of analyzing the methylation status of a CpG site along a DNA molecule comprising:
   (a) contacting the DNA with a CpG-methylation-sensitive methyltransferase enzyme in the presence of a co-factor which is labeled with a detectable moiety under conditions which brings about covalent transfer of said detectable moiety from said co-factor to said DNA; and
   (b) detecting said detectable moiety, wherein the presence of the detectable moiety is indicative of a non-methylated CpG site,
   and wherein the method further comprises determining the number of repeats of a DNA sequence of said DNA by covalently attaching to the DNA molecule an additional detectable moiety which labels a sequence of said DNA which is not a CpG site using a DNA labeling agent and wherein said DNA labeling agent is i) a sequence-specific CpG-methylation-insensitive DNA methyltransferase (DNA MTase) or ii) a sequence specific nicking enzyme in a NLR reaction or both i) and ii), and wherein the detectable moiety of step (a) is not identical to said additional detectable moiety.

12. The method of claim 11, wherein said DNA labeling agent is a sequence specific nicking enzyme in a NLR reaction.

13. The method of claim 11, wherein said DNA labeling agent is a sequence specific CpG-methylation insensitive DNA MTase.

14. The method of claim 13, wherein said CpG-methylation insensitive DNA methyltransferase has a double-stranded recognition sequence which does not contain the 5'-CG-3' sequence.

15. The method of claim 14, wherein said CpG-methylation insensitive DNA methyltransferase is a DNA adenine methylase (Dam); or a M.EcoDam or a derivative thereof; or a M.BseCI or a derivative thereof.

16. The method of claim 1, wherein said nick label repair reaction further includes a DNA polymerase enzyme.

17. The method of claim 16, wherein said nick label repair reaction includes a DNA polymerase enzyme and a DNA ligase enzyme.

18. The method of claim 11, wherein said nick label repair reaction further includes a DNA polymerase enzyme.

19. The method of claim 18, wherein said nick label repair reaction includes a DNA polymerase enzyme and a DNA ligase enzyme.

20. The method of claim 1, said determining said number of repeats and said determining said CpG methylation status are performed on the same, single DNA molecule.

21. The method of claim 11, wherein said contacting said DNA with said CpG methylation sensitive methyltransferase enzyme, stretching said DNA molecule, detecting said detectable moiety and said covalently attaching said additional detectable moiety are performed on the same, single DNA molecule.

22. The method of claim 1, wherein said analyzing said CpG methylation status is done without subjecting the DNA molecule to fragmentation.

23. The method of claim 1, wherein said repeats are D4Z4 repeats and said disease is facioscapulohumeral muscular dystrophy (FSHD).

* * * * *

SEQUENCE LISTING

```
<160> NUMBER OF SEQ ID NOS: 1

<210> SEQ ID NO 1
<211> LENGTH: 3220
<212> TYPE: DNA
<213> ORGANISM: Homo sapiens
<220> FEATURE:
<221> NAME/KEY: misc_feature
<223> OTHER INFORMATION: D4Z4 repeat nucleic acid sequence

<400> SEQUENCE: 1
cccgggccag agctctcctg cctctccacc agcccacccc gccgcctgac cgcccctcc      60 ccacccccca cccccaccc ccggaaaacg cgtcgtcccc tgggctgggt ggagacccc     120 gtcccgcgaa acaccgggcc ccgcgcagcg tccgggcctg acaccgctcc gccggctcgc    180
ctcctcctgt cgccccggg ccaccgtcgc ccgcccgccc gggcccctgc gggccctgc     240 agccgcccag ctgccagcac gggcggctgg cggcggaacg cagaccccag gcccggcgca    300
caccggggac gctgagcgtt ccaggcggga gggaaggcgg gcagagatgg agagaggaac    360
gggagagact agagggggcgg aagggacgtt aggagggagg cagggaggca gggaggcagg    420
gaggaacgga gggagagaca gagcgacgca gggactgggg gcggggccga gggagccggg    480
gacggacggg gggaggaagg cagggaggaa aagcggtcct cggcctccgg gagtagcggg    540
accgcccgcc tccgggaaaa cggtcagcgt ccggcgcggg ctgagggctg ggcccacagc    600
```

-continued

```
cgccgcgccg gccggcgggg caccacccat tcgccccggt tccggggccc agggagtggg      660
cggtttcctc cgggacaaaa gaccgggact cgggttgccg tcgggtcttc acccgcgcgg      720
ttcacagacc gcacatcccc aggctgagcc ctgcaacgcg gcgcgaggcc cacagacccg      780
gccacggagg agccacacgc aggacgacgg aggcgtgatt ttggtttccg agtggctttg      840
ccctcccgaa ggcggcctgt tgctcacgtc tctccggccc ccgaaaggct ggccatgccg      900
actgtttgct cccggagctc tgcggcaccc ggaaacatgc agggaagggt gcaagcccgg      960
catggtgcct tcgctctcct tgccaggttc caaacccgcc acactgcaga ctcccccacg     1020
ttgccgcacg cgggaatcca tcgtcaggcc atcacgccgg ggaggcatct cctctctggg     1080
gtctcgctct ggtcttctac gtggaaatga acgagagcca cacgcctgcg tgtgcgagac     1140
cgtcccggca acggcgacgc ccacaggcat tgcctccttc acggagagag ggcctggcac     1200
actcaagact cccacggagg ttcagttcca cactcccctc caccctccca ggctggtttc     1260
tccctgctgc cgacgcgtgg gagcccagag agcggcttcc cgttcccgcg ggatccctgg     1320
agaggtccgg agagccggcc cccgaaacgc gccccctcc cccctccccc ctctcccct      1380 tcctcttcgt ctctccggcc ccaccaccac caccgccacc acgcctcccc caccaccccc     1440
ccccccaccc accaccacca ccaccacccc gccggccggc cccaggcctc gacgccctgg     1500
gtcccttccg gggtggggcg ggctgtccca gggggctca ccgccattca tgaaggggtg      1560
gagcctgcct gcctgtgggc ctttacaagg gcggctggct ggctggctgg ctgtccgggc     1620
aggcctcctg gctgcacctg ccgcagtgca cagtccggct gaggtgcacg ggagcccgcc     1680
ggcctctctc tgcccgcgtc cgtccgtgaa attccggccg gggctcaccg cgatggccct     1740
cccgacaccc tcggacagca ccctcccgc ggaagcccgg ggacgaggac ggccacggag      1800
actcgtttgg accccgagcc aaagcgaggc cctgcgagcc tgctttgagc ggaacccgta     1860
cccgggcatc gccaccagag aacggctggc ccaggccatc ggcattccgg agcccagggt     1920
ccagatttgg tttcagaatg agaggtcacg ccagctgagg cagcaccggc gggaatctcg     1980
gccctggccc gggagacgcg gcccgccaga aggccggcga aagcggaccg ccgtcaccgg     2040
atcccagacc gccctgctcc tccgagcctt tgagaaggat cgcttttccag gcatcgccgc     2100 ccgggaggag ctggccagag agacgggcct cccggagtcc aggattcaga tctggtttca     2160
gaatcgaagg gccaggcacc cgggacaggg tggcagggcg cccgcgcagg caggcggcct     2220
gtgcagcgcg gcccccggcg ggggtcaccc tgctccctcg tgggtcgcct tcgcccacac     2280
cggcgcgtgg ggaacggggc ttccgcacc ccacgtgccc tgcgcgcctg gggctctccc      2340
acagggggct ttcgtgagcc aggcagcgag ggccgccccc gcgctgcagc ccagccaggc     2400
cgcgccggca gaggggggtct cccaacctgc cccggcgcgc ggggatttcg cctacgccgc     2460
cccggctcct ccggagccgg ggcgctctcc caccctcagg ctcctcggtg gcctccgcac     2520
ccgggcaaaa gccggggagga ccgggacccg cagcgcgacg gcctgccggg ccctgcgcg      2580 gtggcacagc ctgggcccgc tcaagcgggg ccgcaggcca aggggtgctt gcgccaccca     2640
cgtcccaggg gagtccgtgg tggggctggg gccggggtcc ccaggtcgcc ggggcggcgt     2700
gggaacccca agccggggca gctccacctc cccagcccgc gccccgggga cgcctccgcc     2760
tccgcgcggc aggggcagat gcaaggcatc ccggcgccct cccaggcgct ccaggagccg     2820
gcgccctggt ctgcactccc ctgccggcctg ctgctggatg agctcctggc gagcccggag     2880
tttctgcagc aggcgcaacc tctcctagaa acgcgaggccc cggggagct ggaggcctcg      2940 gaagaggcgc ctcgctggaa gcacccctca gcgaggaaga ataccgggct ctgctggagg     3000
```

```
agctttagga cgcggggttg ggacggggtc gggtggttcg gggcagggcg gtggcctctc    3060
tttcgcgggg aacacctggc tggctacgga ggggcgtgtc tccgcccgc ccctccacc     3120 gggctgaccg gcctgggatt cctgccttct aggtccaggc ccggtgagag actccacacc   3180
gcggagaact gccattcttt cctgggcatc ccggggatcc                          3220
```